US010655142B1

(12) United States Patent
Shi et al.

(10) Patent No.: US 10,655,142 B1
(45) Date of Patent: May 19, 2020

(54) MOLECULAR MARKERS LINKED TO DISEASE RESISTANCE IN SOYBEAN

(71) Applicant: Syngenta Participations AG, Basel (CH)

(72) Inventors: Ainong Shi, Fayetteville, AR (US);
Harish T. Gandhi, Medchal Mandal (IN); Becky Welsh Breitinger, Research Triangle Park, NC (US); Zhanyou Xu, Slater, IA (US); Roger L. McBroom; Harikrishnan Ramasubramaniam, Bay, AR (US)

(73) Assignee: Syngenta Participations AG, Basel (CH)

( * ) Notice: Subject to any disclaimer, the term of this patent is extended or adjusted under 35 U.S.C. 154(b) by 224 days.

(21) Appl. No.: 15/000,388

(22) Filed: Jan. 19, 2016

Related U.S. Application Data

(63) Continuation of application No. 13/486,705, filed on Jun. 1, 2012, now abandoned.

(60) Provisional application No. 61/492,104, filed on Jun. 1, 2011.

(51) Int. Cl.
*C12N 15/82* (2006.01)
*A01H 1/04* (2006.01)

(52) U.S. Cl.
CPC ......... *C12N 15/8279* (2013.01); *A01H 1/04* (2013.01)

(58) Field of Classification Search
None
See application file for complete search history.

(56) References Cited

U.S. PATENT DOCUMENTS

2006/0135758 A1   6/2006   Wu

OTHER PUBLICATIONS

Weng et al 2001 The Journal of Heredity 92:442-446 (Year: 2001).*
Yang et al 2010 Journal of Heredity 101:757-768 (Year: 2010).*
Van et al. Discovery of single nucleotide polymorphisms in soybean using primers designed from ESTs. Euphytica 39: 147-157.
Weng et al. 2001. Mapping genes conferring resistance to Phytophthora root for soybean, Rsp1a and Rsp7. The Journal of Heredity 92(5): 442-446.

* cited by examiner

*Primary Examiner* — Brent T Page
(74) *Attorney, Agent, or Firm* — R. Kody Jones

(57) ABSTRACT

The present invention relates to methods and compositions for identifying, selecting and/or producing a soybean plant or germplasm having a Rps1 resistance allele and resistance to *Phytophthora sojae*. A soybean plant, part thereof and/or germplasm that has been identified, selected and/or produced by any of the methods of the present invention is also provided.

6 Claims, No Drawings
Specification includes a Sequence Listing.

SEQUENCE LISTING

<160> NUMBER OF SEQ ID NOS: 40

<210> SEQ ID NO 1
<211> LENGTH: 501

```
<212> TYPE: DNA
<213> ORGANISM: Glycine max
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (251)..(251)
<223> OTHER INFORMATION: n is a or t
<220> FEATURE:
<221> NAME/KEY: misc_feature
<222> LOCATION: (362)..(362)
<223> OTHER INFORMATION: n is a, c, g, or t

<400> SEQUENCE: 1
aacctccacc ttcaatttgg gtgccnacac ttgaacctgg cagctcagtt tttgtttccc    60
cagaaggatt tgtctgcaac aactggggtt cataactcgg tccagccatn gatgtgggta   120
ctggtatctg agcgnccacg ccacctgtca ctggtgccgt tgctggaacc tgtgcttgag   180
atagtacggt cattaggagc tgagccaaaa gtacctgcgg atcattatca ccttgttgga   240
cttgaacatt nattgcatta gacagagcat tgatgtcagg tgggtaaatt gcttgaagcc   300
ctaagagtgc cccagacaga gcttgctgct ggtgctggcc tactccagat gaagcacgcc   360
tnagttttga taggtgtttt tcccagcca catgactctg gtaaacaact tgtgactcac    420
atttaacatc acacagctca catctaaaag acatagtttg tgcaggttcc actggcttag   480
aaccatcatt agttctcatg t                                             501

<210> SEQ ID NO 2
<211> LENGTH: 501
<212> TYPE: DNA
<213> ORGANISM: Glycine max
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (251)..(251)
<223> OTHER INFORMATION: n is a or c
<220> FEATURE:
<221> NAME/KEY: misc_feature
<222> LOCATION: (303)..(303)
<223> OTHER INFORMATION: n is a, c, g, or t

<400> SEQUENCE: 2
atacaaattt gtccacttgt ctatgattgc tatggctgat acaagtacct attttttgac    60
cacacattcc aaatttgtag gagcaataca tgacaataag acaacaantt ggttttccca   120
catcatcgca catatttctt gttgctttct acaattgatc tcattttgga gaacttggcc   180
atcactcagg tcacgtcctc ttcaacagga aacccaagat gagtccaatg atgccaacaa   240
gaactacgta natgaatggt acaccgccgc ggcttctgcc ggcatcacgc ctcaaaagct   300
ccngcacaca aaagattcca aaccaatcca ttattttcca tgagaataat aattgcatgt   360
gatgtattta ttgacttctt catcaaacat ttaaccatca tggcaagtaa tgactacagt   420
tttacttcaa aaagaaaaa gtaatgacta aagtttgact gcactactag tactctaatg   480
```
aaaaatgatc taggatgcgt t                                              501

<210> SEQ ID NO 3
<211> LENGTH: 501
<212> TYPE: DNA
<213> ORGANISM: Glycine max
<220> FEATURE:
<221> NAME/KEY: misc_feature
<222> LOCATION: (251)..(251)
<223> OTHER INFORMATION: n is g or c
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t

<400> SEQUENCE: 3
ttattaatat gacgatgcaa atacgatttt aaagacaaac tgttttaaat ctcttataaa    60
aaaaaacttt tataaacgaa atcaaaaact tttagatcaa gtatcgtttc gagtcaacta   120
catagtgaat gcagcactgt tttgctagca attcagtaaa agagtattcc aattaactac   180
ttgcctagaa tttgaatgga actatgtatt agtagttcca aaatatatgg ttccttcgat   240
aatgtttctt nagatacttc tgtatcaaaa cacggtaagt ccatttcctc tgtgtcttga   300
actcaaaaaa tgcttcagaa ctcatttgaa antcccctt acctaaggcc tgatacacaa   360
aaggatctgt taataatcgc ggagaatcat ccaagttcat tttgtttaga gcaaantcca   420
agtttcttcc aagccttcta tccaagtatg catcaactac acacccaaaa gtcactagat   480
caggnatgac nttctcatgt t                                              501

<210> SEQ ID NO 4
<211> LENGTH: 501
<212> TYPE: DNA
<213> ORGANISM: Glycine max
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (251)..(251)
<223> OTHER INFORMATION: n is c or g
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (497)..(497)
<223> OTHER INFORMATION: n is a, c, g, or t

<400> SEQUENCE: 4

```
gacacgtgtc ttcctcccca gcttctttct gtgcgccgcc acaccngaca aactaaacac    60
cgtcgctgcc gcgttcgcct tggcctccca cgtggncacc cgatatcaaa acctcggcga   120
tgccgtttaa cgcgccntca gtctccatta tcttagtctt attcgcttcc aatattgaca   180
tgttcaaaat cgtcgtgacg gcgttaacct gcaggctcgg nttctccgca ttaaggaacc   240
gaaccaaaac nggaatcgct cccgcttcgg ctatacaagc tcggctatcc gaatctgtct   300
tngccaacac ccgaagctcg taaacgacgc cgtttgtgtc ttcaacactc aaaggaacgt   360
taacgttatc nttttccctt cccttgagct tgttgatcaa aaacgacacc gtcattcgcg   420
tggcttctaa tgcggctttg ttggtaactc caccgttgag tttccctgta tccgtttctg   480
cttcgaaggg gattctntgc t                                              501
```

<210> SEQ ID NO 5
<211> LENGTH: 501
<212> TYPE: DNA
<213> ORGANISM: Glycine max
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (251)..(251)
<223> OTHER INFORMATION: n is c or a
<220> FEATURE:
<221> NAME/KEY: misc_feature
<222> LOCATION: (374)..(374)
<223> OTHER INFORMATION: n is a, c, g, or t

<400> SEQUENCE: 5

```
aaacnggaat cgctcccgct tcggctatac aagctcggct atccgaatct gtcttngcca    60 acaccccgaag ctcgtaaacg acgccgtttg tgtcttcaac actcaaagga acgttaacgt   120
tatcnttttc ccttcccttg agcttgttga tcaaaaacga caccgtcatt cgcgtggctt   180
ctaatgcggc tttgttggta actccaccgt tgagtttccc tgtatccgtt tctgcttcga   240
aggggattct ntgctcgcgg caccacgctg ttatcatgtt ccgcaggacg cgattgggga   300
ttaggtcgct gtgtgataac gtttgacccg tttttggaca cgtgttgtgt ccagaatcca   360
tccagagctt gatngataca cgatcgtatg tttgtcctgt tgccaccacg acgggatcgc   420
gcatgagctc taggcttatc ggacaccggt aatccgccgg aatcgccagc tccgacgact   480
ggttccgccg cagagtgacg g                                              501
```

<210> SEQ ID NO 6
<211> LENGTH: 501
<212> TYPE: DNA
<213> ORGANISM: Glycine max
<220> FEATURE:

```
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (295)..(295)
<223> OTHER INFORMATION: n is a, c, g, or t

<400> SEQUENCE: 6
tgttgaaggt tacatgccaa aacagacctc tttgtgtgtt ttgatgctac attacacaga    60
gaatggcttt tttcctcaag cacagactnt atgggagcag ctcctaaata gctcttttgt   120
tccttctgtt caattcattt caagattatt tgatgcttat gcaaaacatg gaaattcga    180 tgaggtgatc gataccctac gatangtaga tatgaggaat ttcagtattt tacccgatgt   240
ttactcnttg nccatatctt gttttggaag agaaggacag cttgagttga tggangatat   300
ggcaaaggaa atggcttcaa gaggtatcca tatctgttct agaactgcta atgctttcct   360
tttgtattgt agtattttg gttctttgaa agagatggag aatgcgtatg ccgccttaa    420 aaaatctaga tttctgatag agaagggagc gattcgcgct gtggcctctg cgtatataaa   480
ggagagaaaa ttctacgaat t                                             501

<210> SEQ ID NO 7
<211> LENGTH: 501
<212> TYPE: DNA
<213> ORGANISM: Glycine max
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (367)..(367)
<223> OTHER INFORMATION: n is a, c, g, or t

<400> SEQUENCE: 7
gaatcgctcc cttctctatc agaaatctag attttttaag gcggccatac gcattctcca    60
tctctttcaa agaaccaaaa atactacaat acaaaaggaa agcattagca gttctagaac   120
agatatggat acctcttgaa gccatttcct ttgccatatc ntccatcaac tcaagctgtc   180
cttctcttcc aaaacaagat atggncaang agtaaacatc gggtaaaata ctgaaattcc   240
tcatatctac ntatcgtagg gtatcgatca cctcatcgaa tttcccatgt tttgcataag   300
catcaaataa tcttgaaatg aattgaacag aaggaacaaa agagctattt aggagctgct   360
```

```
cccatanagt ctgtgcttga ggaaaaaagc cattctctgt gtaatgtagc atcaaaacac    420
acaaagaggt ctgttttggc atgtaacctt caacattcat atcatgaaaa accccatcag    480
attgatgaat cattctttc c                                               501
```

```
<210> SEQ ID NO 8
<211> LENGTH: 501
<212> TYPE: DNA
<213> ORGANISM: Glycine max
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (251)..(251)
<223> OTHER INFORMATION: n is a or g
<220> FEATURE:
<221> NAME/KEY: misc_feature
<222> LOCATION: (406)..(406)
<223> OTHER INFORMATION: n is a, c, g, or t

<400> SEQUENCE: 8
```

```
caaacggtgg ccagcttctc agtgaagcaa aggtttgaaa gaggggaaca tgctacatgg     60
gtgagcacaa tatatgaaaa aagatttggt ttttaatgtt ttttgaagat ggggnggcag    120
tgcatgattg attttggatg aaggtgtttg ttagatgtta ttagaagaaa attttgttta    180
tatatatatn ttttttttcct tttactttgg aggtgttgtt tacgttggaa ggaagattca   240
ggggaggtgg ntttgttgtt ggatttaaag agttttttttt ctcctaattc taggtaggta   300
ttgtaatgag ggacttggtt atagtttaag gtttgcagca tgagttacag agaaaggaac   360
aaagggaagg gagaagagaa ggaatatgag aacagtacta ctgtgngatt ggattcaaaa   420
tcagtgagtc acaacaatgg ttcaatagaa gaggagctgc taacaattga tgagaatctt   480
ctgattgacc ccaaactgtt g                                              501
```

```
<210> SEQ ID NO 9
<211> LENGTH: 19
<212> TYPE: DNA
<213> ORGANISM: Artificial
<220> FEATURE:
<223> OTHER INFORMATION: Amplification primer sequence

<400> SEQUENCE: 9
acccacctga catcaatgc                                                  19
```

```
<210> SEQ ID NO 10
<211> LENGTH: 18
<212> TYPE: DNA
<213> ORGANISM: Artificial
<220> FEATURE:
<223> OTHER INFORMATION: Amplification primer sequence

<400> SEQUENCE: 10
gtgccgttgc tggaacct                                                   18
```

```
<210> SEQ ID NO 11
<211> LENGTH: 20
<212> TYPE: DNA
<213> ORGANISM: Artificial
<220> FEATURE:
```

<223> OTHER INFORMATION: Amplification primer sequence

<400> SEQUENCE: 11
gagcttttga ggcgtgatgc                                                   20

<210> SEQ ID NO 12
<211> LENGTH: 22
<212> TYPE: DNA
<213> ORGANISM: Artificial
<220> FEATURE:
<223> OTHER INFORMATION: Amplification primer sequence

<400> SEQUENCE: 12
gagtccaatg atgccaacaa ga                                                22

<210> SEQ ID NO 13
<211> LENGTH: 23
<212> TYPE: DNA
<213> ORGANISM: Artificial
<220> FEATURE:
<223> OTHER INFORMATION: Amplification primer sequence

<400> SEQUENCE: 13
cacagaggaa atggacttac cgt                                               23

<210> SEQ ID NO 14
<211> LENGTH: 20
<212> TYPE: DNA
<213> ORGANISM: Artificial
<220> FEATURE:
<223> OTHER INFORMATION: Amplification primer sequence

<400> SEQUENCE: 14
tgaatgcagc actgttttgc                                                   20

<210> SEQ ID NO 15
<211> LENGTH: 21
<212> TYPE: DNA
<213> ORGANISM: Artificial
<220> FEATURE:
<223> OTHER INFORMATION: Amplification primer sequence

<400> SEQUENCE: 15
gccgagcttg tatagccgaa g                                                 21

<210> SEQ ID NO 16
<211> LENGTH: 19
<212> TYPE: DNA
<213> ORGANISM: Artificial
<220> FEATURE:
<223> OTHER INFORMATION: Amplification primer sequence

<400> SEQUENCE: 16
tcgtgacggc gttaacctg                                                    19

<210> SEQ ID NO 17
<211> LENGTH: 23
<212> TYPE: DNA
<213> ORGANISM: Artificial
<220> FEATURE:
<223> OTHER INFORMATION: Amplification primer sequence

<400> SEQUENCE: 17
cgtcctgcgg aacatgataa cag                                               23

-continued

```
<210> SEQ ID NO 18
<211> LENGTH: 20
<212> TYPE: DNA
<213> ORGANISM: Artificial
<220> FEATURE:
<223> OTHER INFORMATION: Amplification primer sequence

<400> SEQUENCE: 18
tggcttctaa tgcggctttg                                            20

<210> SEQ ID NO 19
<211> LENGTH: 23
<212> TYPE: DNA
<213> ORGANISM: Artificial
<220> FEATURE:
<223> OTHER INFORMATION: Amplification primer sequence

<400> SEQUENCE: 19
catcaactca agctgtcctt ctc                                        23

<210> SEQ ID NO 20
<211> LENGTH: 25
<212> TYPE: DNA
<213> ORGANISM: Artificial
<220> FEATURE:
<223> OTHER INFORMATION: Amplification primer sequence

<400> SEQUENCE: 20
gcttatgcaa aacatgggaa attcg                                      25

<210> SEQ ID NO 21
<211> LENGTH: 25
<212> TYPE: DNA
<213> ORGANISM: Artificial
<220> FEATURE:
<223> OTHER INFORMATION: Amplification primer sequence

<400> SEQUENCE: 21
gcttatgcaa aacatgggaa attcg                                      25

<210> SEQ ID NO 22
<211> LENGTH: 23
<212> TYPE: DNA
<213> ORGANISM: Artificial
<220> FEATURE:
<223> OTHER INFORMATION: Amplification primer sequence

<400> SEQUENCE: 22
catcaactca agctgtcctt ctc                                        23

<210> SEQ ID NO 23
<211> LENGTH: 24
<212> TYPE: DNA
<213> ORGANISM: Artificial
<220> FEATURE:
<223> OTHER INFORMATION: Amplification primer sequence

<400> SEQUENCE: 23
aaccaagtcc ctcattacaa tacc                                       24

<210> SEQ ID NO 24
<211> LENGTH: 25
<212> TYPE: DNA
<213> ORGANISM: Artificial
<220> FEATURE:
<223> OTHER INFORMATION: Amplification primer sequence
```

```
<400> SEQUENCE: 24
tgtttacgtt ggaaggaaga ttcag                                          25

<210> SEQ ID NO 25
<211> LENGTH: 19
<212> TYPE: DNA
<213> ORGANISM: Artificial
<220> FEATURE:
<223> OTHER INFORMATION: Marker probe sequence

<400> SEQUENCE: 25
ctaatgcaat aaatgttca                                                 19

<210> SEQ ID NO 26
<211> LENGTH: 18
<212> TYPE: DNA
<213> ORGANISM: Artificial
<220> FEATURE:
<223> OTHER INFORMATION: Marker probe sequence

<400> SEQUENCE: 26
tctgtctaat gcaattaa                                                  18

<210> SEQ ID NO 27
<211> LENGTH: 17
<212> TYPE: DNA
<213> ORGANISM: Artificial
<220> FEATURE:
<223> OTHER INFORMATION: Marker probe sequence

<400> SEQUENCE: 27
tgtaccattc atgtacg                                                   17

<210> SEQ ID NO 28
<211> LENGTH: 18
<212> TYPE: DNA
<213> ORGANISM: Artificial
<220> FEATURE:
<223> OTHER INFORMATION: Marker probe sequence

<400> SEQUENCE: 28
cggtgtacca ttcattta                                                  18

<210> SEQ ID NO 29
<211> LENGTH: 20
<212> TYPE: DNA
<213> ORGANISM: Artificial
<220> FEATURE:
<223> OTHER INFORMATION: Marker probe sequence

<400> SEQUENCE: 29
tgatacagaa gtatctcaag                                                20

<210> SEQ ID NO 30
<211> LENGTH: 20
<212> TYPE: DNA
<213> ORGANISM: Artificial
<220> FEATURE:
<223> OTHER INFORMATION: Marker probe sequence

<400> SEQUENCE: 30
ttgatacaga agtatctgaa                                                20

<210> SEQ ID NO 31
<211> LENGTH: 14
```

<212> TYPE: DNA
<213> ORGANISM: Artificial
<220> FEATURE:
<223> OTHER INFORMATION: Marker probe sequence

<400> SEQUENCE: 31
agcgattccc gttt                                                          14

<210> SEQ ID NO 32
<211> LENGTH: 15
<212> TYPE: DNA
<213> ORGANISM: Artificial
<220> FEATURE:
<223> OTHER INFORMATION: Marker probe sequence

<400> SEQUENCE: 32
agcgattccg gtttt                                                         15

<210> SEQ ID NO 33
<211> LENGTH: 15
<212> TYPE: DNA
<213> ORGANISM: Artificial
<220> FEATURE:
<223> OTHER INFORMATION: Marker probe sequence

<400> SEQUENCE: 33
ccgcgagcag agaat                                                         15

<210> SEQ ID NO 34
<211> LENGTH: 16
<212> TYPE: DNA
<213> ORGANISM: Artificial
<220> FEATURE:
<223> OTHER INFORMATION: Marker probe sequence

<400> SEQUENCE: 34
ccgcgagcat agaatc                                                        16

<210> SEQ ID NO 35
<211> LENGTH: 19
<212> TYPE: DNA
<213> ORGANISM: Artificial
<220> FEATURE:
<223> OTHER INFORMATION: Marker probe sequence

<400> SEQUENCE: 35
caaaacaaga tatggccaa                                                     19

<210> SEQ ID NO 36
<211> LENGTH: 19
<212> TYPE: DNA
<213> ORGANISM: Artificial
<220> FEATURE:
<223> OTHER INFORMATION: Marker probe sequence

<400> SEQUENCE: 36
ccaaaacaag atatggtca                                                     19

<210> SEQ ID NO 37
<211> LENGTH: 16
<212> TYPE: DNA
<213> ORGANISM: Artificial
<220> FEATURE:
<223> OTHER INFORMATION: Marker probe sequence

<400> SEQUENCE: 37

-continued

```
accctacgat acgtag                                                  16

<210> SEQ ID NO 38
<211> LENGTH: 18
<212> TYPE: DNA
<213> ORGANISM: Artificial
<220> FEATURE:
<223> OTHER INFORMATION: Marker probe sequence

<400> SEQUENCE: 38
taccctacga tatgtaga                                                18

<210> SEQ ID NO 39
<211> LENGTH: 17
<212> TYPE: DNA
<213> ORGANISM: Artificial
<220> FEATURE:
<223> OTHER INFORMATION: Marker probe sequence

<400> SEQUENCE: 39
atccaacaac aaaccca                                                 17

<210> SEQ ID NO 40
<211> LENGTH: 19
<212> TYPE: DNA
<213> ORGANISM: Artificial
<220> FEATURE:
<223> OTHER INFORMATION: Marker probe sequence

<400> SEQUENCE: 40
taaatccaac aacaaatcc                                               19
```

MOLECULAR MARKERS LINKED TO DISEASE RESISTANCE IN SOYBEAN

CROSS REFERENCES TO RELATED APPLICATIONS

The presently disclosed subject matter claims the benefit of U.S. Provisional Patent Application Ser. No. 61/492,104, filed Jun. 1, 2011; and U.S. patent application Ser. No. 13/486,705 filed Jun. 1, 2013 the disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 9207-48PR_ST25.txt, 15,619 bytes in size, generated on May 9, 2011 and filed via EFS-Web, is provided in lieu of a paper copy. This Sequence Listing is hereby incorporated by reference into the specification for its disclosures.

FIELD OF THE INVENTION

The present invention relates to compositions and methods for identifying, selecting and producing *Phytophthora* resistant soybean plants. More particularly, this invention relates to markers that are associated with a particular region of Chromosome 3 of *Glycine* sp. (previously called Linkage Group (LG) N), which is associated with resistance to *Phytophthora sojae*, can be used for producing soybean lines with improved resistance to *P. sojae*.

BACKGROUND

Soybean (*Glycine max* L. Merr) is a major cash crop in North America and around the globe. Soybean oil is one of the most widely used edible oils, and soybeans are used worldwide as animal feed and for human consumption and for industrial purposes. *P. sojae* is an oomycete pathogen, which was first described in Ohio and shortly thereafter in Indiana and North Carolina (Suhovecky and Schmitthenner, Ohio Farm Home Res. 40:85-86 (1955)). *P. sojae* has now been reported to be present in all soybean growing regions of the U.S. as well as other parts of the world (Zhang et al. *MPMI.* 19(12):1302-1310(2006); (Wrather et al. *Can. J. Plant Pathol.* 23:115-121 (2001)). Symptoms of *Phytophthora* Root Rot (PRR) caused by *P. sojae* include yellowing and wilting of leaves and browning of lower stems and branches (Demirbas et al. *Crop Sci.* 41:1220-1227 (2001)). PRR is the second leading cause of yield loss in soybean in the United States. In 1998, yield losses due to PRR, in the U.S. and Argentina, the top soybean producing countries, were 1149 and 92 thousand metric tons respectively (Id.). PRR results in annual worldwide soybean crop losses of S1 to S2 billion (Zhang et al. MPMI. 19(12):1302-1310(2006)).

To date, eight loci, Rps1, Rps2, Rps3, Rps4, Rps5, Rps6, Rps7, and Rps8, have been identified which provide race-specific resistance to *P. sojae*. These loci were mapped to chromosomes 3, 16, 13, 18, 18, 18, 3 and 13 (previously called molecular linkage groups (MLG) N, J, F, G, G, G, N, and F, respectively) and simple sequence repeat (SSR) markers were reported to be linked to these genes (Burnham et al. *Crop Sci.* 43:101-105 (2003)); Diers et al. *Crop Sci.* 32:377-383 (1992); Gordon et al. *Crop Sci.* 46:168-173 (2005); Gordon et al. Phytopathology 97:113-118 (2007); Lohnes and Schmitthenner, *Crop Sci.* 37:555-556 (1997); Sandhu et al. *Genetics* 168:2157-2167 (2004); Sandhu et al. *J. Hered.* 96(5):536-541 (2005); Weng et al. *J. Hered.* 92:442-446 (2001)).

The Rps1 locus is complex having multiple alleles including Rps1a, Rps1b, Rps1c, Rps1d, and Rps1k (Bernard and Cremeens, *Soybean Genet. Newsletter* 8:40-42 (1981); Lohnes and Schmitthenner, *Crop Sci.* 37:555-556 (1997); Ferro et al., *Crop Sci.* 46:2427-2436 (2006); Weng et al. *J. Hered.* 92:442-446 (2001)). Rps1a was mapped on chromosome 3 (previously called MLG N), flanked by SSR markers, Satt159 (0.7 cM) and Satt009 (3.2 cM) (Weng et al. *J. Hered.* 92:442-446 (2001)). The recombination value was reported to be 0.16 and 0.13 between the gene Rps1 and Satt159 and Satt152 in another research (Demirbas et al. *Crop Sci.* 41:1220-1227 (2001)). Additionally, Satt530 and Satt584 were also reported to be linked to Rps1, Rps1b, and Rps1c with recombination values of 0.00 and 0.00, 0.12 and 0.20, and 0.14 and 0.21, respectively (Id.).

Rps1-k, first identified in the cultivar Kingwa (Bernard and Cremeens *Soybean Genet. Newsletter* 8:40-42 (1981)), has been used extensively used gene in breeding *Phytophthora*-resistant soybean cultivars (Schmitthenner et al., *Plant Dis.* 78:269-276(1994)). High resolution genetic and physical maps have been constructed for the Rps1-k region, and the gene has been isolated through positional cloning and transformation experiments and its sequence has been published in GenBank with the accession EU450800 (Bhattacharyya et al. *Plant Mol. Biol.* 34:255-264 (1997); Gao et al. *Mol. Plant Microbe Interact.* 18:1035-1045 (2005); Kasuga et al. *Mol. Plant Microbe Interact.* 10:1035-1044 (1997)). Although previously Rps1-k was considered to be a single gene, two functional units/genes, Rps1-k-1 and Rps1-k-2 were cloned from the Rps1-k locus. Rps1-k-1 is located between 17988 bp to 21677 bp and Rps1-k-2 is located between 42421 bp to 46170 bp of the GenBank accession EU450800. The Rps1-k gene sequences are disclosed in U.S. Pat. No. 7,256,323B1 to Bhattacharyya et al.

Currently, the presence or absence of Rps1 alleles is determined by phenotyping against different races of *P. sojae* in the greenhouse. Thus, the present invention overcomes the shortcomings in the art by providing markers associated with the different Rps1 alleles, thereby allowing for a more precise and faster characterization of soybean cultivars for the presence or absence Rps1 alleles by molecular analysis rather than by more time consuming greenhouse phenotypic analysis.

SUMMARY OF THE INVENTION

Compositions and methods for identifying, selecting and producing soybean plants having Rps1 resistance alleles are provided. Soybean plants and/or soybean germplasms and/or parts thereof having Rps1 resistance alleles are also provided.

Accordingly, in one aspect of this invention, a method of identifying and/or selecting a soybean plant or germplasm having an Rps1 resistance allele is provided, the method comprising: detecting, in a soybean plant or germplasm, the presence of a genetic marker associated with an Rps1 resistance allele, wherein said genetic marker comprises (1) a T allele at nucleotide 251 of SEQ ID NO:1 (SY2723AQ); (2) a C allele at nucleotide 251 of SEQ ID NO:3 (SY2724AQ); (3) a G allele at nucleotide 251 of SEQ ID NO:4 (SY2726BQ); (4) an A allele at nucleotide 251 of SEQ ID NO:5 (SY2726DQ); (5) an A allele at nucleotide 251 of SEQ ID NO:6 (SY2724BQ); (6) an A allele at nucleotide 251 of SEQ ID NO:7 (SY2724CQ); (7) an A allele at nucleotide 251 of SEQ ID NO:8 (SY2725AQ); (8) a T allele at nucleotide 251 of SEQ ID NO:1 (SY2723AQ) and a C allele at nucleotide 251 of SEQ ID NO:2 (SY2721AQ); (9) a T allele at nucleotide 251 of SEQ ID NO:1 (SY2723AQ) and a G allele at nucleotide 251 of SEQ ID NO:3 (SY2724AQ); (10) a T allele at nucleotide 251 of SEQ ID NO:1 (SY2723AQ) and a C allele at nucleotide 251 of SEQ ID NO:5 (SY2726DQ); (11) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (12) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (13) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (14) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (15) a C allele at nucleotide 251 of SEQ ID NO:3 (SY2724AQ) and an A allele at nucleotide 251 of SEQ ID NO:7 (SY2724CQ); (16) a G allele at nucleotide 251 of SEQ ID NO:4 (SY2726BQ) and an A allele at nucleotide 251 of SEQ ID NO:7 (SY2724CQ); (17) wherein the SNP is an A allele at nucleotide 251 of SEQ ID NO:5 (SY2726DQ) and an A allele at nucleotide 251 of SEQ ID NO:7 (SY2724CQ); (18) is a C allele at nucleotide 251 of SEQ ID NO:3 (SY2724AQ) and an A allele at nucleotide 251 of SEQ ID NO:6 (SY2724BQ); (19) a G allele at nucleotide 251 of SEQ ID NO:4 (SY2726BQ) and an A allele at nucleotide 251 of SEQ ID NO:6 (SY2724BQ); (20) an A allele at nucleotide 251 of SEQ ID NO:5 (SY2726DQ) and an A allele at nucleotide 251 of SEQ ID NO:6 (SY2724BQ); (21) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (22) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (23) an A allele at nucleotide 251 of SEQ ID NO:8 (SY2725AQ) and an A allele at nucleotide 251 of SEQ ID NO:7 (SY2724CQ); (24) an A allele at nucleotide 251 of SEQ ID NO:8 (SY2725AQ) and an A allele at nucleotide 251 of SEQ ID NO:6 (SY2724BQ); (25) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (26) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (27) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (28) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (29) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (30) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (31) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (32) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ); (33) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (34) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (35) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (36) a T allele at nucleotide 251 of SEQ ID NO:1 (SY2723AQ) and a C allele at nucleotide 251 of SEQ ID NO:3 (SY2724AQ); (37) a T allele at nucleotide 251 of SEQ ID NO:1 (SY2723AQ) and an A allele at nucleotide 251 of SEQ ID NO:5 (SY2726DQ), (38) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (39) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (40) a T allele at nucleotide 251 of SEQ ID NO:1 (SY2723AQ) and an A allele at nucleotide 251 of SEQ ID NO:8 (SY2725AQ); (41) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (42) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (43) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (44) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (45) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (46) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (47) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (48) C allele at nucleotide 251 of SEQ ID NO:3 (SY2724AQ) and an A allele at nucleotide 251 of SEQ ID NO:8 (SY2725AQ); (49) an A allele at nucleotide 251 of SEQ ID NO:5 (SY2726DQ) and an A allele at nucleotide 251 of SEQ ID NO:8 (SY2725AQ); (50) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (51) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (52) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (53) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (54) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (55) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (56) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (57) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (58) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (59) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination of (1)-(59) above, thereby identifying and/or selecting a soybean plant or germplasm having an Rps1 resistance allele. The genetic markers (e.g., SNPs, combinations of SNPs) of the present invention are associated with the Rps1 resistance alleles Rps1-a, Rps1-c, Rps1-k, or any combination thereof.

In other aspects, the present invention provides a method of producing a soybean plant having an Rps1 resistance allele, the method comprising: (a) detecting, in a soybean germplasm, the presence of a genetic marker associated with an Rps1 resistance allele, wherein said genetic marker comprises (1) a T allele at nucleotide 251 of SEQ ID NO:1 (SY2723AQ); (2) a C allele at nucleotide 251 of SEQ ID NO:3 (SY2724AQ); (3) a G allele at nucleotide 251 of SEQ ID NO:4 (SY2726BQ); (4) an A allele at nucleotide 251 of SEQ ID NO:5 (SY2726DQ); (5) an A allele at nucleotide 251 of SEQ ID NO:6 (SY2724BQ); (6) an A allele at nucleotide 251 of SEQ ID NO:7 (SY2724CQ); (7) an A allele at nucleotide 251 of SEQ ID NO:8 (SY2725AQ); (8) a T allele at nucleotide 251 of SEQ ID NO:1 (SY2723AQ) and a C allele at nucleotide 251 of SEQ ID NO:2 (SY2721AQ); (9) a T allele at nucleotide 251 of SEQ ID NO:1 (SY2723AQ) and a G allele at nucleotide 251 of SEQ ID NO:3 (SY2724AQ); (10) a T allele at nucleotide 251 of SEQ ID NO:1 (SY2723AQ) and a C allele at nucleotide 251 of SEQ ID NO:5 (SY2726DQ); (11) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (12) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (13) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (14) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (15) a C allele at nucleotide 251 of SEQ ID NO:3 (SY2724AQ) and an A allele at nucleotide 251 of SEQ ID NO:7 (SY2724CQ); (16) a G allele at nucleotide 251 of SEQ ID NO:4 (SY2726BQ) and an A allele at nucleotide 251 of SEQ ID NO:7 (SY2724CQ); (17) wherein the SNP is an A allele at nucleotide 251 of SEQ ID NO:5 (SY2726DQ) and an A allele at nucleotide 251 of SEQ ID NO:7 (SY2724CQ); (18) is a C allele at nucleotide 251 of SEQ ID NO:3 (SY2724AQ) and an A allele at nucleotide 251 of SEQ ID NO:6 (SY2724BQ); (19) a G allele at nucleotide 251 of SEQ ID NO:4 (SY2726BQ) and an A allele at nucleotide 251 of SEQ ID NO:6 (SY2724BQ); (20) an A allele at nucleotide 251 of SEQ ID NO:5 (SY2726DQ) and an A allele at nucleotide 251 of SEQ ID NO:6 (SY2724BQ); (21) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (22) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (23) an A allele at nucleotide 251 of SEQ ID NO:8 (SY2725AQ) and an A allele at nucleotide 251 of SEQ ID NO:7 (SY2724CQ); (24) an A allele at nucleotide 251 of SEQ ID NO:8 (SY2725AQ) and an A allele at nucleotide 251 of SEQ ID NO:6 (SY2724BQ); (25) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (26) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (27) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (28) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (29) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (30) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (31) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (32) a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:6 (SY2724BQ), (33) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (34) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (35) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (36) a T allele at nucleotide 251 of SEQ ID NO:1 (SY2723AQ) and a C allele at nucleotide 251 of SEQ ID NO:3 (SY2724AQ); (37) a T allele at nucleotide 251 of SEQ ID NO:1 (SY2723AQ) and an A allele at nucleotide 251 of SEQ ID NO:5 (SY2726DQ), (38) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (39) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (40) a T allele at nucleotide 251 of SEQ ID NO:1 (SY2723AQ) and an A allele at nucleotide 251 of SEQ ID NO:8 (SY2725AQ); (41) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (42) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (43) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (44) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (45) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (46) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (47) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (48) C allele at nucleotide 251 of SEQ ID NO:3 (SY2724AQ) and an A allele at nucleotide 251 of SEQ ID NO:8 (SY2725AQ); (49) an A allele at nucleotide 251 of SEQ ID NO:5 (SY2726DQ) and an A allele at nucleotide 251 of SEQ ID NO:8 (SY2725AQ); (50) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (51) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (52) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (53) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (54) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (55) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (56) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (57) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (58) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (59) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination of (1)-(59) above; and (b) producing a soybean plant from said soybean germplasm, thereby producing a soybean plant having an Rps1 resistance allele.

A further aspect of this invention provides a method of introgressing an Rps1 resistance allele into a soybean germplasm that is lacking the Rps1 resistance allele, the method comprising: (a) crossing a donor parental soybean line comprising a genetic marker associated with an Rps1 resistance allele with a recurrent parental soybean line that lacks said marker to produce progeny; (b) selecting progeny comprising said marker and backcrossing said progeny with the recurrent parental soybean line, wherein said progeny are selected by detecting, in their genomes, the presence of said marker associated with an Rps1 resistance allele, wherein said marker comprises: (1) a T allele at nucleotide 251 of SEQ ID NO:1 (SY2723AQ); (2) a C allele at nucleotide 251 of SEQ ID NO:3 (SY2724AQ); (3) a G allele at nucleotide 251 of SEQ ID NO:4 (SY2726BQ); (4) an A allele at nucleotide 251 of SEQ ID NO:5 (SY2726DQ); (5) an A allele at nucleotide 251 of SEQ ID NO:6 (SY2724BQ); (6) an A allele at nucleotide 251 of SEQ ID NO:7 (SY2724CQ); (7) an A allele at nucleotide 251 of SEQ ID NO:8 (SY2725AQ); (8) a T allele at nucleotide 251 of SEQ ID NO:1 (SY2723AQ) and a C allele at nucleotide 251 of SEQ ID NO:2 (SY2721AQ); (9) a T allele at nucleotide 251 of SEQ ID NO:1 (SY2723AQ) and a G allele at nucleotide 251 of SEQ ID NO:3 (SY2724AQ); (10) a T allele at nucleotide 251 of SEQ ID NO:1 (SY2723AQ) and a C allele at nucleotide 251 of SEQ ID NO:5 (SY2726DQ); (11) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (12) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (13) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (14) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (15) a C allele at nucleotide 251 of SEQ ID NO:3 (SY2724AQ) and an A allele at nucleotide 251 of SEQ ID NO:7 (SY2724CQ); (16) a G allele at nucleotide 251 of SEQ ID NO:4 (SY2726BQ) and an A allele at nucleotide 251 of SEQ ID NO:7 (SY2724CQ); (17) wherein the SNP is an A allele at nucleotide 251 of SEQ ID NO:5 (SY2726DQ) and an A allele at nucleotide 251 of SEQ ID NO:7 (SY2724CQ); (18) is a C allele at nucleotide 251 of SEQ ID NO:3 (SY2724AQ) and an A allele at nucleotide 251 of SEQ ID NO:6 (SY2724BQ); (19) a G allele at nucleotide 251 of SEQ ID NO:4 (SY2726BQ) and an A allele at nucleotide 251 of SEQ ID NO:6 (SY2724BQ); (20) an A allele at nucleotide 251 of SEQ ID NO:5 (SY2726DQ) and an A allele at nucleotide 251 of SEQ ID NO:6 (SY2724BQ); (21) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (22) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (23) an A allele at nucleotide 251 of SEQ ID NO:8 (SY2725AQ) and an A allele at nucleotide 251 of SEQ ID NO:7 (SY2724CQ); (24) an A allele at nucleotide 251 of SEQ ID NO:8 (SY2725AQ) and an A allele at nucleotide 251 of SEQ ID NO:6 (SY2724BQ); (25) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (26) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (27) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (28) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (29) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (30) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (31) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (32) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ), (33) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (34) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (35) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (36) a T allele at nucleotide 251 of SEQ ID NO:1 (SY2723AQ) and a C allele at nucleotide 251 of SEQ ID NO:3 (SY2724AQ); (37) a T allele at nucleotide 251 of SEQ ID NO:1 (SY2723AQ) and an A allele at nucleotide 251 of SEQ ID NO:5 (SY2726DQ), (38) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (39) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (40) a T allele at nucleotide 251 of SEQ ID NO:1 (SY2723AQ) and an A allele at nucleotide 251 of SEQ ID NO:8 (SY2725AQ); (41) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (42) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (43) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (44) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (45) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (46) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (47) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (48) C allele at nucleotide 251 of SEQ ID NO:3 (SY2724AQ) and an A allele at nucleotide 251 of SEQ ID NO:8 (SY2725AQ); (49) an A allele at nucleotide 251 of SEQ ID NO:5 (SY2726DQ) and an A allele at nucleotide 251 of SEQ ID NO:8 (SY2725AQ); (50) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (51) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (52) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (53) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (54) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (55) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (56) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (57) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (58) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (59) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination of (1)-(59) above; (c) backcrossing the selected progeny of (b) with the recurrent parental soybean line to produce further progeny; and (d) repeating steps (b) to (c) one or more times, thereby introgressing the Rps1 resistance allele into the recurrent parental line, and thus introgressing the Rps1 resistance allele into the soybean germplasm that is lacking the Rps1 resistance allele.

Compositions comprising a primer pair capable of amplifying a nucleic acid sample isolated from a maize plant or germplasm to generate a marker associated with an Rps1 resistance allele are also provided. Such compositions may comprise, consist essentially of or consist of one of the amplification primer pairs and/or probes identified in Table 1.

These and other aspects of the invention are set forth in more detail in the description of the invention below.

DETAILED DESCRIPTION

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications and sequences referenced herein are incorporated by reference in their entireties.

Disclosed herein is the identification and design of genetic markers (SNPs and/or combinations of SNPs) that can be used to identify alleles associated with *P. sojae* resistance in soybean.

Therefore, present invention provides compositions and methods for identifying, selecting and/or producing soybean plants having one or more Rps1 *P. sojae* resistance alleles. In addition, the present invention provides soybean plants and/or soybean germplasm having within their genomes one or more SNP markers associated with one or more Rps1 resistance alleles. These SNPs are located within an approximately 1.7 megabase (MB) region of *Glycine* sp. Chromosome 3 (Linkage Group N).

Definitions

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker (e.g., SNP) can mean one marker or a plurality of markers (e.g., 2, 3, 4, 5, 6, 7, 8, 9, 10 and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the phrases "pathogen resistance locus" and "pathogen resistance gene" refer to loci and/or genes that have been associated with pathogen resistance as defined by the markers disclosed herein. In some embodiments of this invention, these loci/genes are present on *Glycine* sp. Chromosome 3 (*Glycine* linkage group N), and linked to the markers represented by SEQ ID NOs: 1-8. Similarly, the phrase "pathogen resistance phenotype" refers to a phenotype the expression of which is influenced by a pathogen resistance locus and/or a pathogen resistance gene.

As used herein, the terms "desired allele," target allele and/or "allele of interest" are used interchangeably to refer to an allele associated with a desired trait. Disclosed herein are exemplary genetic markers (SNP alleles) that are associated with soybean plant resistance or susceptibility to *P. sojae*. For example, the SNP alleles can be associated with Rps1-c, Rps1-a, Rps1-k, or a combination thereof. In some embodiments, the "desired allele" will depend on the gene that is being assayed (e.g., Rps1-a, Rps1-c, Rps1-k or combinations thereof). Thus, for example, when assaying for Rps1-c, the desired allele at SY2726DQ is A. In contrast, when assaying for Rps1-a or Rps1-k, the desired allele at SY2726DQ is C. In a further example, when assaying for Rps1-a, the desired allele at SY2724AQ is G. In contrast, when assaying for Rps1-c, the desired allele at SY2724AQ is C. In a still further example, when assaying for a combination of Rps1-a and Rps1-c, the desired allele at SY2724AQ is C. Alternatively, when assaying for a combination of Rps1-a and Rps1-k, the desired allele at SY2724AQ is G.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with a Rps1 resistance allele" refers to a marker whose presence or absence can be used to predict whether and/or to what extent a plant will display resistance to one or more races of *P. sojae*.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example, in* Techniques et Utilisations des Marqueurs Moleculaires les colloques, Vol. 72, pp. 45-56 (1995); and Openshaw et al., *Marker-assisted Selection in Backcross Breeding, in* Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other cultivars/varieties within the same species.

As used herein, the terms "elite" and/or "elite line" refer to any line that is substantially homozygous and has resulted from breeding and selection for desirable agronomic performance.

As used herein, the term "*P. sojae*-resistant soybean plant or germplasm" refers to a soybean plant or soybean germplasm that is capable of resisting infection by *P. sojae*. When used in reference to germplasm, the term refers to the ability of a plant that arises from that germplasm to resist infection by *P. sojae*.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, as well as plant parts, such as leaves, stems, pollen, or cells that can be cultured into a whole plant.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. Offspring comprising the desired allele can be repeatedly backcrossed to a line having a desired genetic background and selected for the desired allele, with the result being that the desired allele becomes fixed in the desired genetic background. For example, a marker associated with a Rps1 resistance allele may be introgressed from a donor into a recurrent parent that is not resistant to *P. sojae*. The resulting offspring could then be repeatedly backcrossed and selected until the progeny possess the Rps1 resistance allele(s) in the recurrent parent background.

As used herein, the term "linkage" refers to the degree with which one marker locus is associated with another marker locus. The linkage relationship between a molecular marker and a phenotype may be given as a "probability" or "adjusted probability." Linkage can be expressed as a desired limit or range. For example, in some embodiments, any marker is linked (genetically and physically) to any other marker when the markers segregate from each other in the next generation less than 50% of the time, less than 25% of the time, less than 20% of the time, less than 15% of the time, less than 10% of the time, less than 5% of the time, less than 4% of the time, less than 3% of the time, less than 2% of the time, or less than 1% of the time. Thus, in some embodiments, two loci are linked when they are separated by less than about 50, 40, 30, 25, 20, 15, 10, 5, 4, 3, 2, 1, or 0.5 map units or centiMorgans (cM).

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., *P. sojae* resistance. The degree of linkage of a genetic marker to a phenotypic trait is measured, e.g., as a statistical probability of co-segregation of that genetic marker with the phenotype.

Linkage disequilibrium is most commonly assessed using the measure $r^2$, which is calculated using the formula described by Hill and Robertson (*Theor. Appl. Genet.* 38:226 (1968)). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al. (*Nature Reviews Genetics* 3:299 (2002)). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, a SNP allele and/or combination of SNP alleles (haplotype) (Brookes, *Gene* 234:177 (1993)), a gene, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (RE-MAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase internet resource (www.soybase.org). In some embodiments, a genetic marker of this invention is an SNP allele and/or combination of SNP alleles (haplotype), which are associated with Rps1 resistance.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for detecting expressed sequence tags (ESTs) and SSR markers derived from EST sequences and randomly amplified polymorphic DNA (RAPD).

Accordingly, in some embodiments of this invention, a marker corresponds to an amplification product generated by amplifying a *Glycine* sp. nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying *Glycine* sp. genomic DNA with a particular set of primers. In some embodiments, the amplifying is by PCR, and the primers are PCR primers that are designed to hybridize to opposite strands of the *Glycine* sp. genomic DNA in order to amplify a *Glycine* sp. genomic DNA sequence present between the sequences to which the PCR primers hybridize in the *Glycine* sp. genomic DNA. In other embodiments, a marker that "corresponds to" an amplified fragment is a marker that has the same sequence of one of the strands of the amplified fragment.

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Non-limiting examples of probes of this invention include SEQ ID NOs:25-40.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of markers can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of a primer can depend on many factors, including, but not limited to temperature and composition (A/T vs. G/C content) of the primer.

In the context of amplification primers, these are typically provided as a pair of bi-directional primers consisting of one forward and one reverse primer or provided as a pair of forward primers as commonly used in the art of DNA amplification such as in PCR amplification.

As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

As used herein, the term "probe" refers to a single-stranded oligonucleotide sequence that will form a hydrogen-bonded duplex with a complementary sequence in a target nucleic acid sequence analyte or its cDNA derivative.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and for polynucleotide sequence BLASTN can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where the variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seeds and/or a plant cell. A plant cell is a cell of a plant, taken from a plant, or derived through culture from a cell taken from a plant.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue cultures from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "soybean" refers to a plant, and any part thereof, of the genus *Glycine* including, but not limited to, *Glycine* max.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of Fls, F2s and the like. Thus, an F1 can be a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "reference sequence" refers to a defined nucleotide sequence used as a basis for nucleotide sequence comparison (e.g., Chromosome 3 of *Glycine max* cultivar Williams 82). The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in a locus or loci.

Genetic Mapping

Genetic loci correlating with particular phenotypes, such as resistance to *P. sojae*, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with Rps1 resistance alleles and thus, associated with resistance to particular races of *P. sojae*. Detection of these markers and/or other linked markers can be used to identify, select and/or produce plants having Rps1 resistance alleles, and thus, having resistance to *P. sojae* and/or to eliminate plants from breeding programs or from planting that do not have a Rps1 resistance allele and are not resistant to *P. sojae*.

Markers Associated with an Rps1 Resistance Allele

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) *Genomics* 20:176-183.

The recombination frequencies of genetic markers on different chromosomes and/or in different linkage groups are generally 50%. Between genetic markers located on the same chromosome or in the same linkage group, the recombination frequency generally depends on the physical distance between the markers on a chromosome. A low recombination frequency typically corresponds to a low genetic distance between markers on a chromosome. Comparison of all recombination frequencies among a set of genetic markers results in the most logical order of the genetic markers on the chromosomes or in the linkage groups. This most logical order can be depicted in a linkage map. A group of adjacent or contiguous markers on the linkage map that is associated with an increased level of resistance to a disease (e.g., to a reduced incidence of acquiring the disease upon infectious contact with the disease agent and/or a reduced lesion growth rate upon establishment of infection) can provide the position of a locus associated with resistance to that disease. The present invention provides SNP markers and/or combination of SNP markers that can be used in various aspects of the presently disclosed subject matter as set forth herein.

Thus, the SNP markers provided herein can be used for detecting the presence of one or more Rps1 resistance alleles in soybean plant or germplasm, and can therefore be used in methods involving marker-assisted breeding and selection of *P. sojae*-resistant soybean plants/soybean plants having one or more Rps1 resistance alleles.

In some embodiments, methods for detecting the presence of an SNP in a soybean plant or germplasm can comprise providing a oligonucleotide or polynucleotide capable of hybridizing under stringent hybridization conditions to a nucleotide sequence of a SNP disclosed herein, contacting the oligonucleotide or polynucleotide with genomic nucleic acid (or a fragment thereof, including, but not limited to a restriction fragment thereof) of the soybean plant or germplasm, and determining the presence of the SNP by the specific hybridization of the oligonucleotide or polynucleotide to the soybean genomic nucleic acid (or the fragment thereof).

Accordingly, SNP markers associated with Rps1 resistance alleles are identified herein. The SNP markers of the present invention are described herein with respect to their position in Chromosome 3 (linkage group N) of the soybean genome (e.g., *Glycine max* L. cultivar Williams 82) (reference sequence found at the Soybase database, www.soybase.org). Thus, Table 1 provides each of the markers of this invention with their corresponding name, sequence identifier (SEQ ID NO), the location of the SNP on Chromosome 3 of soybean cultivar Williams 82 (8× public build; SoyBase internet resource (www.soybase.org/SequenceIntro.php)), the target resistance allele and non-target allele at that location, the gene that is tagged by the marker and associated amplification primers and marker probes.

(transferred from the donor soybean plant). In other embodiments, the recipient soybean plant can susceptible to all *P. sojae* races. This allows the breeder to develop soybean plants having resistance to one or more races of *P. sojae*. The transfer of the nucleotide sequence can be performed by any of the methods described herein.

Thus, methods for identifying, selecting and/or producing a soybean plant or germplasm comprising an Rps1 resistance allele can comprise detecting the presence of a genetic marker associated with an Rps1 resistance allele. The SNP marker can be detected in any sample taken from the soybean plant or germplasm, including, but not limited to, the whole plant or germplasm, a portion of said plant or germplasm (e.g., a cell, leaf, seed, etc, from said plant or germplasm) or a nucleotide sequence from said plant or germplasm.

TABLE 1

Description of the SNP markers and related data.

| | | Marker Sequence (SEQ ID NO) (location of allele) | Position in Reference Sequence | Marker Alleles | | | Amplification Primer Pair (SEQ ID NO) | Marker Probes (SEQ ID NO) |
|---|---|---|---|---|---|---|---|---|
| Reference Sequence | Name | | | Allele 1 | Allele 2 | Associated Gene | | |
| *Glycine max* L. cultivar Williams 82 (Gm03) | SY2723AQ | 1 (nt 251) | 3,832,550 | T | A | Rps1-a | 9, 10 | 25/26 |
| | SY2721AQ | 2 (nt 251) | 3,634,150 | C | A | Rps1-a, Rps1-c | 11, 12 | 27/28 |
| | SY2724AQ | 3 (nt 251) | 4,474,011 | C | G | Rps1-c | 13, 14 | 29/30 |
| | SY2726BQ | 4 (nt 251) | 4,632,793 | G | C | Rps1-c | 15, 16 | 31/32 |
| | SY2726DQ | 5 (nt 251) | 4,633,039 | A | C | Rps1-c | 17, 18 | 33/34 |
| | SY2724BQ | 6 (nt 251) | 4,474,754 | A | G | Rps1c, Rps1-k | 19, 20 | 35/36 |
| | SY2724CQ | 7 (nt 251) | 4,474,791 | A | G | Rps1c, Rps1-k | 21, 22 | 37/38 |
| | SY2725AQ | 8 (nt 251) | 4,531,558 | A | G | Rps1-k | 23, 24 | 39/40 |

As shown in Table 1, the SNP markers of this invention are associated with the Rps1 resistance alleles, Rps1-a, Rps1-c, and Rps1-k. In some embodiments of this invention, the SNP marker can be associated with more than one Rps1 allele. In some embodiments, as described herein, a combination of SNPs can be used to detect the presence of an Rps1 resistance allele.

In further embodiments, a marker of this invention can include any marker linked to the aforementioned markers. Linked markers may be determined, for example, by using resources available on the SoyBase internet resource (www.soybase.org).

The presently disclosed subject matter thus also relates to methods for identifying, selecting, and/or producing soybean plants having an Rps1 resistance allele comprising detecting in a donor soybean plant the presence of a genetic marker associated with an Rps1 resistance allele and/or a genetic marker associated with *P. sojae* resistance as described herein and transferring the nucleotide sequence comprising the at least one genetic marker thus detected from the donor soybean plant to a *P. sojae*-recipient soybean plant. It is noted that the recipient soybean plant can be resistant to certain *P. sojae* races and susceptible to other *P. sojae* races. Typically, the recipient soybean plant is at least susceptible to the race of *P. sojae* for which the transfer of the nucleotide sequence comprising the genetic marker (associated with an Rps1 resistance allele) confers resistance Accordingly, in one aspect of the present invention, a method of identifying and/or selecting a soybean plant or germplasm having an Rps1 resistance allele is provided, the method comprising: detecting, in a soybean plant or germplasm, the presence of a genetic marker associated with an Rps1 resistance allele, wherein said marker comprises, consists essentially of, or consists of (1) a T allele at nucleotide 251 of SEQ ID NO:1 (SY2723AQ); (2) a C allele at nucleotide 251 of SEQ ID NO:3 (SY2724AQ); (3) a G allele at nucleotide 251 of SEQ ID NO:4 (SY2726BQ); (4) an A allele at nucleotide 251 of SEQ ID NO:5 (SY2726DQ); (5) an A allele at nucleotide 251 of SEQ ID NO:6 (SY2724BQ); (6) an A allele at nucleotide 251 of SEQ ID NO:7 (SY2724CQ); (7) an A allele at nucleotide 251 of SEQ ID NO:8 (SY2725AQ); (8) a T allele at nucleotide 251 of SEQ ID NO:1 (SY2723AQ) and a C allele at nucleotide 251 of SEQ ID NO:2 (SY2721AQ); (9) a T allele at nucleotide 251 of SEQ ID NO:1 (SY2723AQ) and a G allele at nucleotide 251 of SEQ ID NO:3 (SY2724AQ); (10) a T allele at nucleotide 251 of SEQ ID NO:1 (SY2723AQ) and a C allele at nucleotide 251 of SEQ ID NO:5 (SY2726DQ); (11) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (12) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (13) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (14) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (15) a C allele at nucleotide 251 of SEQ ID NO:3 (SY2724AQ) and an A allele at nucleotide 251 of SEQ ID NO:7 (SY2724CQ); (16) a G allele at nucleotide 251 of SEQ ID NO:4 (SY2726BQ) and an A allele at nucleotide 251 of SEQ ID NO:7 (SY2724CQ); (17) wherein the SNP is an A allele at nucleotide 251 of SEQ ID NO:5 (SY2726DQ) and an A allele at nucleotide 251 of SEQ ID NO:7 (SY2724CQ); (18) is a C allele at nucleotide 251 of SEQ ID NO:3 (SY2724AQ) and an A allele at nucleotide 251 of SEQ ID NO:6 (SY2724BQ); (19) a G allele at nucleotide 251 of SEQ ID NO:4 (SY2726BQ) and an A allele at nucleotide 251 of SEQ ID NO:6 (SY2724BQ); (20) an A allele at nucleotide 251 of SEQ ID NO:5 (SY2726DQ) and an A allele at nucleotide 251 of SEQ ID NO:6 (SY2724BQ); (21) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (22) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (23) an A allele at nucleotide 251 of SEQ ID NO:8 (SY2725AQ) and an A allele at nucleotide 251 of SEQ ID NO:7 (SY2724CQ); (24) an A allele at nucleotide 251 of SEQ ID NO:8 (SY2725AQ) and an A allele at nucleotide 251 of SEQ ID NO:6 (SY2724BQ); (25) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (26) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (27) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (28) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (29) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (30) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (31) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (32) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ), (33) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (34) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (35) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (36) a T allele at nucleotide 251 of SEQ ID NO:1 (SY2723AQ) and a C allele at nucleotide 251 of SEQ ID NO:3 (SY2724AQ); (37) a T allele at nucleotide 251 of SEQ ID NO:1 (SY2723AQ) and an A allele at nucleotide 251 of SEQ ID NO:5 (SY2726DQ), (38) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (39) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (40) a T allele at nucleotide 251 of SEQ ID NO:1 (SY2723AQ) and an A allele at nucleotide 251 of SEQ ID NO:8 (SY2725AQ); (41) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (42) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (43) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (44) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (45) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (46) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (47) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (48) C allele at nucleotide 251 of SEQ ID NO:3 (SY2724AQ) and an A allele at nucleotide 251 of SEQ ID NO:8 (SY2725AQ); (49) an A allele at nucleotide 251 of SEQ ID NO:5 (SY2726DQ) and an A allele at nucleotide 251 of SEQ ID NO:8 (SY2725AQ); (50) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (51) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (52) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (53) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (54) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (55) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (56) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (57) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (58) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (59) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination of (1)-(59) above, thereby identifying and/or selecting a soybean plant or germplasm having an Rps1 resistance allele.

In a further aspect, a method is provided for identifying and/or selecting a *P. sojae*-resistant soybean plant or germplasm, the method comprising: detecting, in a soybean plant or germplasm, the presence of a genetic marker associated with an Rps1 allele conferring resistance to *P. sojae*, wherein the genetic marker comprises, consists essentially of, or consists of (1) a T allele at nucleotide 251 of SEQ ID NO:1 (SY2723AQ); (2) a C allele at nucleotide 251 of SEQ ID NO:3 (SY2724AQ); (3) a G allele at nucleotide 251 of SEQ ID NO:4 (SY2726BQ); (4) an A allele at nucleotide 251 of SEQ ID NO:5 (SY2726DQ); (5) an A allele at nucleotide 251 of SEQ ID NO:6 (SY2724BQ); (6) an A allele at nucleotide 251 of SEQ ID NO:7 (SY2724CQ); (7) an A allele at nucleotide 251 of SEQ ID NO:8 (SY2725AQ); (8) a T allele at nucleotide 251 of SEQ ID NO:1 (SY2723AQ) and a C allele at nucleotide 251 of SEQ ID NO:2 (SY2721AQ); (9) a T allele at nucleotide 251 of SEQ ID NO:1 (SY2723AQ) and a G allele at nucleotide 251 of SEQ ID NO:3 (SY2724AQ); (10) a T allele at nucleotide 251 of SEQ ID NO:1 (SY2723AQ) and a C allele at nucleotide 251 of SEQ ID NO:5 (SY2726DQ); (11) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (12) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (13) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (14) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (15) a C allele at nucleotide 251 of SEQ ID NO:3 (SY2724AQ) and an A allele at nucleotide 251 of SEQ ID NO:7 (SY2724CQ); (16) a G allele at nucleotide 251 of SEQ ID NO:4 (SY2726BQ) and an A allele at nucleotide 251 of SEQ ID NO:7 (SY2724CQ); (17) wherein the SNP is an A allele at nucleotide 251 of SEQ ID NO:5 (SY2726DQ) and an A allele at nucleotide 251 of SEQ ID NO:7 (SY2724CQ); (18) is a C allele at nucleotide 251 of SEQ ID NO:3 (SY2724AQ) and an A allele at nucleotide 251 of SEQ ID NO:6 (SY2724BQ); (19) a G allele at nucleotide 251 of SEQ ID NO:4 (SY2726BQ) and an A allele at nucleotide 251 of SEQ ID NO:6 (SY2724BQ); (20) an A allele at nucleotide 251 of SEQ ID NO:5 (SY2726DQ) and an A allele at nucleotide 251 of SEQ ID NO:6 (SY2724BQ); (21) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (22) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (23) an A allele at nucleotide 251 of SEQ ID NO:8 (SY2725AQ) and an A allele at nucleotide 251 of SEQ ID NO:7 (SY2724CQ); (24) an A allele at nucleotide 251 of SEQ ID NO:8 (SY2725AQ) and an A allele at nucleotide 251 of SEQ ID NO:6 (SY2724BQ); (25) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (26) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (27) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (28) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (29) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (30) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (31) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (32) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ), (33) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (34) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (35) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (36) a T allele at nucleotide 251 of SEQ ID NO:1 (SY2723AQ) and a C allele at nucleotide 251 of SEQ ID NO:3 (SY2724AQ); (37) a T allele at nucleotide 251 of SEQ ID NO:1 (SY2723AQ) and an A allele at nucleotide 251 of SEQ ID NO:5 (SY2726DQ), (38) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (39) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (40) a T allele at nucleotide 251 of SEQ ID NO:1 (SY2723AQ) and an A allele at nucleotide 251 of SEQ ID NO:8 (SY2725AQ); (41) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (42) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (43) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (44) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (45) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (46) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (47) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (48) C allele at nucleotide 251 of SEQ ID NO:3 (SY2724AQ) and an A allele at nucleotide 251 of SEQ ID NO:8 (SY2725AQ); (49) an A allele at nucleotide 251 of SEQ ID NO:5 (SY2726DQ) and an A allele at nucleotide 251 of SEQ ID NO:8 (SY2725AQ); (50) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (51) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (52) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (53) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (54) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (55) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (56) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (57) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (58) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (59) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination of (1)-(59) above, thereby identifying and/or selecting a *P. sojae*-resistant soybean plant or germplasm.

Methods for identifying and/or selecting a soybean plant or germplasm comprising an Rps1 resistance allele and methods for identifying and/or selecting a *P. sojae*-resistant soybean plant or germplasm can comprise detecting the presence of a marker or a combination of markers associated with an Rps1 resistance allele as described herein (i.e., Rps1-a, Rps1-c, Rps1-k, or any combination thereof).

Thus, in some embodiments, the present invention provides methods of identifying and/or selecting a soybean plant or germplasm having an Rps1-a resistance allele and/or a *P. sojae*-resistant soybean plant or germplasm, the methods comprising: detecting, in a soybean plant or germplasm, the presence of a genetic marker associated with an Rps1-a resistance allele, wherein said genetic marker comprises: (1) a T allele at nucleotide 251 of SEQ ID NO:1 (SY2723AQ); (2) a T allele at nucleotide 251 of SEQ ID NO:1 (SY2723AQ) and a C allele at nucleotide 251 of SEQ ID NO:2 (SY2721AQ); (3) a T allele at nucleotide 251 of SEQ ID NO:1 (SY2723AQ) and a G allele at nucleotide 251 of SEQ ID NO:3 (SY2724AQ); (4) a T allele at nucleotide 251 of SEQ ID NO:1 (SY2723AQ) and a C allele at nucleotide 251 of SEQ ID NO:5 (SY2726DQ); (5) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (6) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (7) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (8) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ), or any combination thereof, thereby identifying and/or selecting a soybean plant or germplasm and/or a *P. sojae*-resistant soybean plant or germplasm having an Rps1-a resistance allele.

In other embodiments, the present invention provides a method of identifying and/or selecting a soybean plant or germplasm having an Rps1-c resistance allele and/or a *Phytophthora sojae*-resistant soybean plant or germplasm, the method comprising: detecting, in a soybean plant or germplasm, the presence of a genetic marker associated with an Rps1-c resistance allele, wherein said marker comprises: (1) a C allele at nucleotide 251 of SEQ ID NO:3 (SY2724AQ); (2) a G allele at nucleotide 251 of SEQ ID NO:4 (SY2726BQ); (3) an A allele at nucleotide 251 of SEQ ID NO:5 (SY2726DQ); (4) a C allele at nucleotide 251 of SEQ ID NO:3 (SY2724AQ) and an A allele at nucleotide 251 of SEQ ID NO:7 (SY2724CQ); (5) a G allele at nucleotide 251 of SEQ ID NO:4 (SY2726BQ) and an A allele at nucleotide 251 of SEQ ID NO:7 (SY2724CQ); (6) wherein the SNP is an A allele at nucleotide 251 of SEQ ID NO:5 (SY2726DQ) and an A allele at nucleotide 251 of SEQ ID NO:7 (SY2724CQ); (7) is a C allele at nucleotide 251 of SEQ ID NO:3 (SY2724AQ) and an A allele at nucleotide 251 of SEQ ID NO:6 (SY2724BQ); (8) a G allele at nucleotide 251 of SEQ ID NO:4 (SY2726BQ) and an A allele at nucleotide 251 of SEQ ID NO:6 (SY2724BQ); (9) an A allele at nucleotide 251 of SEQ ID NO:5 (SY2726DQ) and an A allele at nucleotide 251 of SEQ ID NO:6 (SY2724BQ); (10) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (11) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); or any combination thereof, thereby identifying and/or selecting a soybean plant or germplasm and/or a *P. sojae*-resistant soybean plant or germplasm having an Rps1-c resistance allele.

In further embodiments, the present invention provides a method of identifying and/or selecting a soybean plant or germplasm and/or a *P. sojae*-resistant soybean plant or germplasm having an Rps1-k resistance allele is provided, the method comprising: detecting, in a soybean plant or germplasm, the presence of a genetic marker associated with an Rps1-k resistance allele, wherein said genetic marker comprises: (1) an A allele at nucleotide 251 of SEQ ID NO:8 (SY2725AQ); (2) an A allele at nucleotide 251 of SEQ ID NO:8 (SY2725AQ) and an A allele at nucleotide 251 of SEQ ID NO:7 (SY2724CQ); (3) an A allele at nucleotide 251 of SEQ ID NO:8 (SY2725AQ) and an A allele at nucleotide 251 of SEQ ID NO:6 (SY2724BQ); (4) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (5) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (6) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (7) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (8) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (9) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (10) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (11) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ), (12) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (13) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (14) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); or any combination thereof, thereby of identifying and/or selecting a soybean plant or germplasm and/or a *P. sojae*-resistant soybean plant or germplasm having an Rps1-k resistance allele.

In additional embodiments, the present invention provides a method of identifying and/or selecting a soybean plant or germplasm and/or a *P. sojae*-resistant soybean plant or germplasm having an Rps1-a resistance allele and an Rps1-c resistance allele, the method comprising: detecting, in a soybean plant or germplasm, the presence of a genetic marker associated with an Rps1-a and an Rps1c resistance allele, wherein said genetic marker comprises: (1) a T allele at nucleotide 251 of SEQ ID NO:1 (SY2723AQ) and a C allele at nucleotide 251 of SEQ ID NO:3 (SY2724AQ); (2) a T allele at nucleotide 251 of SEQ ID NO:1 (SY2723AQ) and an A allele at nucleotide 251 of SEQ ID NO:5 (SY2726DQ), (3) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (4) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); or any combination thereof, thereby identifying and/or selecting a soybean plant or germplasm and/or a *P. sojae*-resistant soybean plant or germplasm having an Rps1-a resistance allele and an Rps1-c resistance allele.

In some embodiments, the present invention provides a method of identifying and/or selecting a soybean plant or germplasm and/or a *P. sojae*-resistant soybean plant or germplasm having an Rps1-a resistance allele and an Rps1-k resistance allele, the method comprising: detecting, in a soybean plant or germplasm, the presence of a genetic marker associated with an Rps1-a and an Rps1 k resistance allele, wherein said genetic marker comprises: (1) a T allele at nucleotide 251 of SEQ ID NO:1 (SY2723AQ) and an A allele at nucleotide 251 of SEQ ID NO:8 (SY2725AQ); (2) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (3) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (4) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (5) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (6) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (7) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (11) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); or any combination thereof, thereby identifying and/or selecting a soybean plant or germplasm and/or a *P. sojae*-resistant soybean plant or germplasm having an Rps1-a resistance allele and an Rps1-k resistance allele.

In some embodiments, the present invention provides a method of identifying and/or selecting a soybean plant or germplasm and/or a *P. sojae*-resistant soybean plant or germplasm having an Rps1-c resistance allele and an Rps1-k resistance allele, the method comprising: detecting, in a soybean plant or germplasm, the presence of a genetic marker associated with an Rps1-c and an Rps1 k resistance allele, wherein said genetic marker comprises: (1) an A allele at nucleotide 251 of SEQ ID NO:6 (SY2724BQ); (2) an A allele at nucleotide 251 of SEQ ID NO:7 (SY2724CQ); (3) C allele at nucleotide 251 of SEQ ID NO:3 (SY2724AQ) and an A allele at nucleotide 251 of SEQ ID NO:8 (SY2725AQ); (4) an A allele at nucleotide 251 of SEQ ID NO:5 (SY2726DQ) and an A allele at nucleotide 251 of SEQ ID NO:8 (SY2725AQ); (5) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (6) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (7) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (8) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (9) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (10) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); or any combination thereof, thereby identifying and/or selecting a soybean plant or germplasm and/or a *P. sojae*-resistant soybean plant or germplasm having an Rps1-c resistance allele and an Rps1-k resistance allele.

In other embodiments, the present invention provides a method of identifying and/or selecting a soybean plant or germplasm and/or a *P. sojae*-resistant soybean plant or germplasm having an Rps1-a resistance allele, an Rps1-c resistance allele and an Rps1-k resistance allele, the method comprising: detecting, in a soybean plant or germplasm, the presence of a genetic marker associated with an Rps1-a, Rps1-c, and an Rps1 k resistance allele, wherein said genetic marker comprises, consists essentially of, or consists of: (1) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (2) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (3) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (4) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (5) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); or any combination thereof, thereby identifying and/or selecting a soybean plant or germplasm and/or a *P. sojae*-resistant soybean plant or germplasm having an Rps1-a resistance allele, an Rps1-c resistance allele and an Rps1-k resistance allele.

In other aspects, the present invention provides a method of identifying and/or selecting a *P. sojae*-susceptible soybean plant or germplasm, the method comprising: detecting, in said soybean plant or germplasm, the presence of a genetic marker associated with an Rps1 susceptible allele, wherein said genetic marker comprises, consists essentially of, or consists of: (1) an A allele at nucleotide 251 of SEQ ID NO:1 (SY2723AQ); (2) an A allele at nucleotide 251 of SEQ ID NO:2 (SY2721AQ); (3) a G allele at nucleotide 251 of SEQ ID NO:3 (SY2724AQ); (4) a C allele at nucleotide 251 of SEQ ID NO:4 (SY2726BQ); (5) a C allele at nucleotide 251 of SEQ ID NO:5 (SY2726DQ); (6) an G allele at nucleotide 251 of SEQ ID NO:6 (SY2724BQ); (7) an G allele at nucleotide 251 of SEQ ID NO:7 (SY2724CQ); (8) a G allele at nucleotide 251 of SEQ ID NO:8 (SY2725AQ); (9) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:3 (SY2724AQ); (10) an A allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (11) an A allele at nucleotide 251 of SEQ ID NO:1 (SY2723AQ), a C allele at nucleotide 251 of SEQ ID NO:5 (SY2726DQ) and a G allele at nucleotide 251 of SEQ ID NO:8 (SY2725AQ); (12) an A allele at nucleotide 251 of SEQ ID NO:1 (SY2723AQ), is a G allele at nucleotide 251 of SEQ ID NO:3 (SY2724AQ) and a G allele at nucleotide 251 of SEQ ID NO:8 (SY2725AQ); or any combination thereof, thereby identifying and/or selecting a *P. sojae*-susceptible soybean plant or germplasm. Thus, for example, by identifying plants having these particular genetic markers these plants can be removed from the breeding population.

Exemplary Assay Primers for Genotyping and/or Amplification

As discussed herein, in some embodiments of this invention, a marker can be identified using amplification products generated by amplifying a *Glycine* sp. nucleic acid with two oligonucleotide primers. In some embodiments, the amplification is by PCR, and the primers are PCR primers that are designed to hybridize to opposite strands of the *Glycine* sp. genomic DNA (e.g., Chromosome 3) in order to amplify a *Glycine* sp. genomic DNA sequence present between the sequences to which the PCR primers hybridize in the

*Glycine* sp. genomic DNA. Methods of amplifying nucleic acids are well known in the art.

Accordingly, in some embodiments of the present invention, a method of identifying and/or selecting a soybean plant or germplasm having an Rps1 resistance allele is provided, the method comprising: detecting, in said soybean plant or germplasm, the presence of a genetic marker associated with the Rps1 resistance allele, wherein said marker is detected in amplification products from a nucleic acid sample isolated from said soybean plant or germplasm using a probe, said amplification products having been produced using pairs of amplification primers wherein said amplification primers and probes have the nucleotide sequences of: (a) SEQ ID NO:9, SEQ ID NO:10, SEQ ID NO:25 and SEQ ID NO:26, respectively for SY2723AQ; (b) SEQ ID NO:11, SEQ ID NO:12, SEQ ID NO:27 and SEQ ID NO:28, respectively for SY2721AQ; (c) SEQ ID NO:13, SEQ ID NO:14, SEQ ID NO:29 and SEQ ID NO:30, respectively for SY2724AQ; (d) SEQ ID NO:15, SEQ ID NO:16, SEQ ID NO:31 and SEQ ID NO:32, respectively for SY2726BQ; (e) SEQ ID NO:17, SEQ ID NO:18, SEQ ID NO:33 and SEQ ID NO:34, respectively for SY2726DQ; (f) SEQ ID NO:19, SEQ ID NO:20, SEQ ID NO:35 and SEQ ID NO:36, respectively for SY2724BQ; (g) SEQ ID NO:21, SEQ ID NO:22, SEQ ID NO:37, and SEQ ID NO:38, respectively for SY2724CQ; (h) SEQ ID NO:23 and SEQ ID NO:24, SEQ ID NO:39, and SEQ ID NO:40, respectively for SY2725AQ, (i) or any combination of (a) through (h) above, thereby identifying and/or selecting a soybean plant or germplasm having an Rps1 resistance allele.

In other embodiments, a method of producing a soybean plant or germplasm having an Rps1 resistance allele is provided, the method comprising: (a) detecting, in said soybean plant or germplasm, the presence of a genetic marker associated with the Rps1 resistance allele, wherein said marker is detected in amplification products from a nucleic acid sample isolated from said soybean plant or germplasm using a probe, said amplification products having been produced using pairs of amplification primers, wherein said amplification primers and probes have the nucleotide sequences of: (a) SEQ ID NO:9, SEQ ID NO:10, SEQ ID NO:25 and SEQ ID NO:26, respectively for SY2723AQ; (b) SEQ ID NO:11, SEQ ID NO:12, SEQ ID NO:27 and SEQ ID NO:28, respectively for SY2721AQ; (c) SEQ ID NO:13, SEQ ID NO:14, SEQ ID NO:29 and SEQ ID NO:30, respectively for SY2724AQ; (d) SEQ ID NO:15, SEQ ID NO:16, SEQ ID NO:31 and SEQ ID NO:32, respectively for SY2726BQ; (e) SEQ ID NO:17, SEQ ID NO:18, SEQ ID NO:33 and SEQ ID NO:34, respectively for SY2726DQ; (f) SEQ ID NO:19, SEQ ID NO:20, SEQ ID NO:35 and SEQ ID NO:36, respectively for SY2724BQ; (g) SEQ ID NO:21, SEQ ID NO:22, SEQ ID NO:37, and SEQ ID NO:38, respectively for SY2724CQ; (h) SEQ ID NO:23 and SEQ ID NO:24, SEQ ID NO:39, and SEQ ID NO:40, respectively for SY2725AQ, (i) or any combination of (a) through (h) above; and (b) producing a soybean plant from said soybean germplasm, thereby producing a soybean plant or germplasm having an Rps1 resistance allele. As the skilled artisan would readily recognize, when combinations of SNPs are detected, then combinations of primers and probes are used.

Marker-Assisted Selection

The subject matter disclosed herein also relates to methods for producing pathogen-resistant soybean plants comprising detecting the presence of a genetic marker associated with pathogen resistance in a donor soybean plant according to the methods as described herein and transferring a nucleic acid sequence comprising at least one genetic marker thus detected from the donor plant to a recipient soybean plant. The transfer of the nucleic acid sequence can be performed by any method known in the art.

Thus, the present invention encompasses methods of plant breeding and methods of selecting/identifying plants, in particular soybean plants, particularly cultivated soybean plants as breeder plants for use in breeding programs or cultivated soybean plants having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a plant of the genus *Glycine* having *P. sojae* resistance comprising detecting in the plant the presence of one or more Rps1 resistance alleles as defined herein. In an exemplary embodiment of the presently disclosed methods for selecting such a plant, the method comprises providing a sample of genomic DNA from a soybean plant; and (b) detecting in the sample of genomic DNA at least one genetic marker associated with *P. sojae* resistance. In some embodiments, the detecting comprises detecting one or more SNPs that are associated with *P. sojae* resistance.

The providing of a sample of genomic DNA from a soybean plant can be performed by standard DNA isolation methods well known in the art.

The detecting of a genetic marker (e.g., SNP, combination of SNPs) can in some embodiments comprise the use of one or more sets of primer pairs (SNP assays) that can be used to produce one or more amplification products that can be used in the detection of genetic markers (SNPs). Such a set of primers can comprise, in some embodiments, nucleotide sequences as set forth in SEQ ID NOs:9-24.

In some embodiments, the detecting of a genetic marker can comprise the use of a nucleic acid probe having a nucleotide base sequence that is substantially complementary to the nucleic acid sequence defining the genetic marker and which nucleic acid probe specifically hybridizes under stringent conditions with a nucleic acid sequence defining the genetic marker. A suitable nucleic acid probe can for instance be a single strand of the amplification product corresponding to the marker. In some embodiments, the detecting of a genetic marker is designed to determine whether a particular allele of a SNP is present or absent in a particular plant.

The presently disclosed subject matter thus also relates to methods for producing pathogen-resistant soybean plants comprising detecting the presence of a genetic marker associated with an Rps1 resistance allele (or a genetic marker associated with *P. sojae* resistance) in a donor soybean plant according to the presently disclosed subject matter as described herein and transferring a nucleotide sequence comprising at least one genetic marker thus detected, or a *P. sojae* resistance-conferring part thereof, from the donor plant to a recipient soybean plant. In particular embodiments, the recipient soybean plant is susceptible to the race of *P. sojae* for which said transferred nucleotide sequence confers resistance. The transfer of the nucleic acid sequence can be performed by any of the methods described herein.

An exemplary embodiment of such a method comprises the transfer of the nucleic acid sequence from a pathogen-resistant donor soybean plant into a recipient soybean plant by crossing the plants by introgression. This transfer can be accomplished by using traditional breeding techniques. Pathogen-resistance loci are introgressed in some embodiments into commercial soybean varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode for the desired trait. As disclosed herein, such identification and selection is based on selection of SNP alleles of this invention or markers associated therewith. MAB can also be used to develop near-isogenic lines (NIL) comprising one or more pathogen resistant alleles of interest, allowing a more detailed study of an effect of such allele(s). MAB is also an effective method for development of backcross inbred line (BIL) populations. Soybean plants developed according to these embodiments can in some embodiments derive a majority of their traits from the recipient plant, and derive pathogen resistance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with pathogen resistance into a recipient soybean plant. The recipient soybean plant may be resistant or susceptible to one or more pathogens or to one or more *P. sojae* races. In some embodiments of the present invention, the recipient soybean plant is susceptible to the *P. sojae* race for which resistance is conferred by trnaferring said nucleic acid sequence associated with pathogen resistance. Thus, for example, inbred pathogen-resistant soybean plant lines can be developed using the techniques of recurrent selection and backcrossing, selfing, and/or dihaploids, or any other technique used to make parental lines. In a method of recurrent selection and backcrossing, pathogen resistance can be introgressed into a target recipient plant (the recurrent parent) by crossing the recurrent parent with a first donor plant, which differs from the recurrent parent (i.e., non-recurrent parent). The recurrent parent is a plant that is non-resistant or has a low level of resistance to one or more pathogens or to a particular race of a pathogen but, in some embodiments, possesses commercially desirable characteristics, such as, but not limited to (additional) disease and/or insect resistance, valuable nutritional characteristics, valuable abiotic stress tolerance (including, but not limited to, drought tolerance, salt tolerance), and the like. In some embodiments, the non-recurrent parent exhibits pathogen resistance and comprises a nucleic acid sequence that is associated with pathogen resistance (e.g., resistance to *P. sojae*). The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence encoding, for example, *P. sojae* resistance or a genetic marker associated with *P. sojae* resistance (e.g., SNPs and SNP combinations described herein). Also, MAB can be used to confirm the results obtained from the quantitative bioassays. In some embodiments, the markers defined herein are suitable to select proper offspring plants by genotypic screening.

Following screening, F1 hybrid plants that exhibit a pathogen-resistant phenotype or, in some embodiments, the genotype, and thus comprise the requisite nucleic acid sequence associated with pathogen resistance, are then selected and backcrossed to the recurrent parent in order to allow for the soybean plant to become increasingly inbred. The process of selecting and backcrossing can be repeated for a number of generations (e.g., for one, two, three, four, five, six, seven, eight, or more generations).

Thus, a marker that demonstrates linkage with a locus affecting a desired phenotypic trait provides a useful tool for selection of the trait in a plant population. This is particularly true where the phenotype is difficult to assay or occurs at a late stage in plant development. Since marker assays are less laborious and take up less physical space than field phenotyping, much larger populations can be assayed, increasing the chances of finding a recombinant plant with the target segment from the donor line that is moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the soybean genome containing increasing densities of public soybean markers has facilitated soybean genetic mapping and MAS. See, e.g. soybeanbreederstoolbox.org, which can be found on the SoyBase internet resource (www.soybase.org).

Of the types genetic marker available, SNPs are some of the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants, in* Plant Genotyping: The DNA Fingerprinting of Plants, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Accordingly, the genetic markers of the present invention can be used in marker-assisted selection methods to identify and/or select and/or produce progeny having an Rps1 resistance allele. Such methods can include crossing a first soybean plant or germplasm with a second soybean plant or germplasm, wherein the first soybean plant or germplasm comprises a SNP marker associated with an Rps1 resistance allele, and selecting a progeny plant that possesses the SNP marker. Therefore, in one embodiment of the present invention, a method of producing a soybean plant having an Rps1 resistance allele is provided, the method comprising: (a) detecting, in a soybean germplasm, the presence of a genetic marker (SNPs or SNP combinations) associated with an Rps1 resistance allele, wherein said marker comprises, consists essentially of, or consists of: (1) a T allele at nucleotide 251 of SEQ ID NO:1 (SY2723AQ); (2) a C allele at nucleotide 251 of SEQ ID NO:3 (SY2724AQ); (3) a G allele at nucleotide 251 of SEQ ID NO:4 (SY2726BQ); (4) an A allele at nucleotide 251 of SEQ ID NO:5 (SY2726DQ); (5) an A allele at nucleotide 251 of SEQ ID NO:6 (SY2724BQ); (6) an A allele at nucleotide 251 of SEQ ID NO:7 (SY2724CQ); (7) an A allele at nucleotide 251 of SEQ ID NO:8 (SY2725AQ); (8) a T allele at nucleotide 251 of SEQ ID NO:1 (SY2723AQ) and a C allele at nucleotide 251 of SEQ ID NO:2 (SY2721AQ); (9) a T allele at nucleotide 251 of SEQ ID NO:1 (SY2723AQ) and a G allele at nucleotide 251 of SEQ ID NO:3 (SY2724AQ); (10) a T allele at nucleotide 251 of SEQ ID NO:1 (SY2723AQ) and a C allele at nucleotide 251 of SEQ ID NO:5 (SY2726DQ); (11) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (12) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (13) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (14) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (15) a C allele at nucleotide 251 of SEQ ID NO:3 (SY2724AQ) and an A allele at nucleotide 251 of SEQ ID NO:7 (SY2724CQ); (16) a G allele at nucleotide 251 of SEQ ID NO:4 (SY2726BQ) and an A allele at nucleotide 251 of SEQ ID NO:7 (SY2724CQ); (17) wherein the SNP is an A allele at nucleotide 251 of SEQ ID NO:5 (SY2726DQ) and an A allele at nucleotide 251 of SEQ ID NO:7 (SY2724CQ); (18) is a C allele at nucleotide 251 of SEQ ID NO:3 (SY2724AQ) and an A allele at nucleotide 251 of SEQ ID NO:6 (SY2724BQ); (19) a G allele at nucleotide 251 of SEQ ID NO:4 (SY2726BQ) and an A allele at nucleotide 251 of SEQ ID NO:6 (SY2724BQ); (20) an A allele at nucleotide 251 of SEQ ID NO:5 (SY2726DQ) and an A allele at nucleotide 251 of SEQ ID NO:6 (SY2724BQ); (21) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (22) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (23) an A allele at nucleotide 251 of SEQ ID NO:8 (SY2725AQ) and an A allele at nucleotide 251 of SEQ ID NO:7 (SY2724CQ); (24) an A allele at nucleotide 251 of SEQ ID NO:8 (SY2725AQ) and an A allele at nucleotide 251 of SEQ ID NO:6 (SY2724BQ); (25) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (26) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (27) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (28) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (29) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (30) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (31) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (32) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ), (33) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (34) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (35) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (36) a T allele at nucleotide 251 of SEQ ID NO:1 (SY2723AQ) and a C allele at nucleotide 251 of SEQ ID NO:3 (SY2724AQ); (37) a T allele at nucleotide 251 of SEQ ID NO:1 (SY2723AQ) and an A allele at nucleotide 251 of SEQ ID NO:5 (SY2726DQ), (38) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (39) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (40) a T allele at nucleotide 251 of SEQ ID NO:1 (SY2723AQ) and an A allele at nucleotide 251 of SEQ ID NO:8 (SY2725AQ); (41) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (42) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (43) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (44) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (45) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (46) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (47) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (48) C allele at nucleotide 251 of SEQ ID NO:3 (SY2724AQ) and an A allele at nucleotide 251 of SEQ ID NO:8 (SY2725AQ); (49) an A allele at nucleotide 251 of SEQ ID NO:5 (SY2726DQ) and an A allele at nucleotide 251 of SEQ ID NO:8 (SY2725AQ); (50) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (51) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (52) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (53) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (54) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (55) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (56) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ); (57) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (58) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (59) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination of (1)-(59) above; and (b) producing a soybean plant from said soybean germplasm, thereby producing a soybean plant having the Rps1 resistance allele.

In other embodiments, the present invention provides a method of introgressing an Rps1 resistance allele into a soybean germplasm that is lacking the Rps1 resistance allele, the method comprising: (a) crossing a donor parental soybean line comprising a genetic marker associated with an Rps1 resistance allele with a recurrent parental soybean line that lacks said marker to produce progeny; (b) selecting progeny comprising said marker and backcrossing said progeny with the recurrent parental soybean line, wherein said progeny are selected by detecting, in their genomes, the presence of the marker associated with an Rps1 resistance allele, wherein the marker comprises: (1) a T allele at nucleotide 251 of SEQ ID NO:1 (SY2723AQ); (2) a C allele at nucleotide 251 of SEQ ID NO:3 (SY2724AQ); (3) a G allele at nucleotide 251 of SEQ ID NO:4 (SY2726BQ); (4) an A allele at nucleotide 251 of SEQ ID NO:5 (SY2726DQ); (5) an A allele at nucleotide 251 of SEQ ID NO:6 (SY2724BQ); (6) an A allele at nucleotide 251 of SEQ ID NO:7 (SY2724CQ); (7) an A allele at nucleotide 251 of SEQ ID NO:8 (SY2725AQ); (8) a T allele at nucleotide 251 of SEQ ID NO:1 (SY2723AQ) and a C allele at nucleotide 251 of SEQ ID NO:2 (SY2721AQ); (9) a T allele at nucleotide 251 of SEQ ID NO:1 (SY2723AQ) and a G allele at nucleotide 251 of SEQ ID NO:3 (SY2724AQ); (10) a T allele at nucleotide 251 of SEQ ID NO:1 (SY2723AQ) and a C allele at nucleotide 251 of SEQ ID NO:5 (SY2726DQ); (11) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (12) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (13) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (14) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (15) a C allele at nucleotide 251 of SEQ ID NO:3 (SY2724AQ) and an A allele at nucleotide 251 of SEQ ID NO:7 (SY2724CQ); (16) a G allele at nucleotide 251 of SEQ ID NO:4 (SY2726BQ) and an A allele at nucleotide 251 of SEQ ID NO:7 (SY2724CQ); (17) wherein the SNP is an A allele at nucleotide 251 of SEQ ID NO:5 (SY2726DQ) and an A allele at nucleotide 251 of SEQ ID NO:7 (SY2724CQ); (18) is a C allele at nucleotide 251 of SEQ ID NO:3 (SY2724AQ) and an A allele at nucleotide 251 of SEQ ID NO:6 (SY2724BQ); (19) a G allele at nucleotide 251 of SEQ ID NO:4 (SY2726BQ) and an A allele at nucleotide 251 of SEQ ID NO:6 (SY2724BQ); (20) an A allele at nucleotide 251 of SEQ ID NO:5 (SY2726DQ) and an A allele at nucleotide 251 of SEQ ID NO:6 (SY2724BQ); (21) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (22) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (23) an A allele at nucleotide 251 of SEQ ID NO:8 (SY2725AQ) and an A allele at nucleotide 251 of SEQ ID NO:7 (SY2724CQ); (24) an A allele at nucleotide 251 of SEQ ID NO:8 (SY2725AQ) and an A allele at nucleotide 251 of SEQ ID NO:6 (SY2724BQ); (25) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7

(SY2724CQ); (26) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (27) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (28) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (29) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (30) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (31) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (32) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ), (33) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (34) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (35) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (36) a T allele at nucleotide 251 of SEQ ID NO:1 (SY2723AQ) and a C allele at nucleotide 251 of SEQ ID NO:3 (SY2724AQ); (37) a T allele at nucleotide 251 of SEQ ID NO:1 (SY2723AQ) and an A allele at nucleotide 251 of SEQ ID NO:5 (SY2726DQ), (38) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (39) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); (40) a T allele at nucleotide 251 of SEQ ID NO:1 (SY2723AQ) and an A allele at nucleotide 251 of SEQ ID NO:8 (SY2725AQ); (41) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (42) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (43) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (44) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (45) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (46) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (47) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (48) C allele at nucleotide 251 of SEQ ID NO:3 (SY2724AQ) and an A allele at nucleotide 251 of SEQ ID NO:8 (SY2725AQ); (49) an A allele at nucleotide 251 of SEQ ID NO:5 (SY2726DQ) and an A allele at nucleotide 251 of SEQ ID NO:8 (SY2725AQ); (50) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (51) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (52) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (53) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (54) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (55) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); (56) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (57) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (58) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (59) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination of (1)-(59) above; (c) backcrossing the selected progeny of (b) with the recurrent parental soybean line to produce further progeny; and (d) repeating steps (b) to (c) one or more times (e.g., one, two, three, four, five, six, seven, eight, nine, ten, or more times), thereby introgressing the Rps1 resistance allele into the recurrent parental line, and thus introgressing the Rps1 resistance allele into the soybean germplasm that is lacking the Rps1 resistance allele.

In some embodiments, a method for introgressing an Rps1 resistance allele into a soybean germplasm lacking the Rps1 resistance allele, comprises: (a) crossing a plant identified, selected or produced according to any of the methods described herein with a second soybean plant lacking the Rps1 resistance allele to produce a segregating population of plants; (b) screening the plants from the segregating population of (a) for the Rps1 resistance allele by detecting, in the plants from the segregating population, the presence of a genetic marker associated with an Rps1 resistance allele as described herein; and (c) selecting a plant from (b) in which the genetic marker is detected, thereby introgressing an Rps1 resistance allele into the soybean germplasm.

In other embodiments of this invention, a method of for producing an inbred soybean plant that is homozygous for an Rps1 resistance allele is provided, the method comprising: (a) selecting a first donor parental line having an Rps1 resistance allele by detecting, in the first donor parental line, a genetic marker associated with an Rps1 resistance allele as described herein; (b) crossing the first donor parental line with a second parental line in hybrid combination to produce a segregating plant population; (c) screening the plants from the segregating population of (b) for the Rps1 resistance allele by detecting, in the plants from the segregating population, the presence of the genetic marker associated with an Rps1 resistance allele as described herein; (d) selecting plants from the population of (c) having the genetic marker associated with an Rps1 resistance allele; and (e) screening the selected plants of (d) to identify an inbred soybean plant that is homozygous for the Rps1 resistance allele, thereby producing an inbred soybean plant that is homozygous for the Rps1 resistance allele.

As described herein, the methods of the present invention encompass detection of Rps1 alleles by detecting the presence of a genetic marker of this invention, wherein the Rps1 resistance alleles comprise Rps1-a, Rps1-c, and/or Rps1-k. Therefore, in some embodiments of this invention, methods of producing a soybean plant having an Rps1-a resistance allele and/or an inbred soybean plant that is homozygous for an Rps1-a resistance allele and/or methods for introgressing an Rps1-a resistance allele into a soybean germplasm lacking the Rps1-a resistance allele are provided, wherein the step of detecting the presence of a genetic marker associated with an Rps1-a resistance allele, comprises detecting the presence of the marker comprising: (1) a T allele at nucleotide 251 of SEQ ID NO:1 (SY2723AQ); (2) a T allele at nucleotide 251 of SEQ ID NO:1 (SY2723AQ) and a C allele at nucleotide 251 of SEQ ID NO:2 (SY2721AQ); (3) a T allele at nucleotide 251 of SEQ ID NO:1 (SY2723AQ) and a G allele at nucleotide 251 of SEQ ID NO:3 (SY2724AQ); (4) a T allele at nucleotide 251 of SEQ ID NO:1 (SY2723AQ) and a C allele at nucleotide 251 of SEQ ID NO:5 (SY2726DQ); (5) a T allele at nucleotide 251 of SEQ ID NO:1 (SY2723AQ), a G allele at nucleotide 251 of SEQ ID NO:3 (SY2724AQ), and a G allele at nucleotide 251 of SEQ ID NO:8 (SY2725AQ); (6) a T allele at nucleotide 251 of SEQ ID NO:1 (SY2723AQ), a C allele at nucleotide 251 of SEQ ID NO:5 (SY2726DQ), and a G allele at nucleotide 251 of SEQ ID NO:8 (SY2725AQ); (7) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and a G allele at nucleotide 251 of SEQ ID NO:7 (SY2724CQ); (8) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); or any combination thereof.

In other embodiments, the present invention provides methods of producing a soybean plant having an Rps1-c resistance allele and/or an inbred soybean plant that is homozygous for an Rps1-c resistance allele and/or methods for introgressing an Rps1-c resistance allele into a soybean germplasm lacking the Rps1-c resistance allele, wherein the step of detecting the presence of a genetic marker associated with an Rps1-c resistance allele, comprises detecting the presence of a genetic marker comprising: (1) a C allele at nucleotide 251 of SEQ ID NO:3 (SY2724AQ); (2) a G allele at nucleotide 251 of SEQ ID NO:4 (SY2726BQ); (3) an A allele at nucleotide 251 of SEQ ID NO:5 (SY2726DQ); (4) a C allele at nucleotide 251 of SEQ ID NO:3 (SY2724AQ) and an A allele at nucleotide 251 of SEQ ID NO:7 (SY2724CQ); (5) a G allele at nucleotide 251 of SEQ ID NO:4 (SY2726BQ) and an A allele at nucleotide 251 of SEQ ID NO:7 (SY2724CQ); (6) wherein the SNP is an A allele at nucleotide 251 of SEQ ID NO:5 (SY2726DQ) and an A allele at nucleotide 251 of SEQ ID NO:7 (SY2724CQ); (7) is a C allele at nucleotide 251 of SEQ ID NO:3 (SY2724AQ) and an A allele at nucleotide 251 of SEQ ID NO:6 (SY2724BQ); (8) a G allele at nucleotide 251 of SEQ ID NO:4 (SY2726BQ) and an A allele at nucleotide 251 of SEQ ID NO:6 (SY2724BQ); (9) an A allele at nucleotide 251 of SEQ ID NO:5 (SY2726DQ) and an A allele at nucleotide 251 of SEQ ID NO:6 (SY2724BQ); (10) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (11) an A allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); or any combination thereof.

In further embodiments, the present invention provides methods of producing a soybean plant having an Rps1-k resistance allele and/or an inbred soybean plant that is homozygous for an Rps1-k resistance allele and/or methods for introgressing an Rps1-k resistance allele into a soybean germplasm lacking the Rps1-k resistance allele, wherein the step of detecting the presence of a genetic marker associated with an Rps1-k resistance allele, comprises detecting the presence of the genetic marker comprising: (1) an A allele at nucleotide 251 of SEQ ID NO:8 (SY2725AQ); (2) an A allele at nucleotide 251 of SEQ ID NO:8 (SY2725AQ) and an A allele at nucleotide 251 of SEQ ID NO:7 (SY2724CQ); (3) an A allele at nucleotide 251 of SEQ ID NO:8 (SY2725AQ) and an A allele at nucleotide 251 of SEQ ID NO:6 (SY2724BQ); (4) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (5) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (6) a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:6 (SY2724BQ); (7) a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:6 (SY2724BQ); (8) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (9) a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:7 (SY2724CQ); (10) a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:6 (SY2724BQ); (11)

a G allele at nucleotide 251 of SEQ ID NO:3 (SY2724AQ), an G allele at nucleotide 251 of SEQ ID NO:8 (SY2725AQ) and an A allele at nucleotide 251 of SEQ ID NO:6 (SY2724BQ), (12) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (13) an A allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ), (14) an A allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); or any combination thereof.

In additional embodiments, the present invention provides methods of producing a soybean plant having an Rps1-a resistance allele and an Rps1-c resistance allele and/or an inbred soybean plant that is homozygous for an Rps1-a resistance allele and an Rps1-c resistance allele and/or methods for introgressing an Rps1-a resistance allele and an Rps1-c resistance allele into a soybean germplasm lacking the Rps1-a and Rps1-c resistance alleles, wherein the step of detecting the presence of a genetic marker associated with an Rps1-a resistance allele and an Rps1-c resistance allele, comprises detecting the presence of the genetic marker comprising: (1) a T allele at nucleotide 251 of SEQ ID NO:1 (SY2723AQ) and a C allele at nucleotide 251 of SEQ ID NO:3 (SY2724AQ); (2) a T allele at nucleotide 251 of SEQ ID NO:1 (SY2723AQ) and an A allele at nucleotide 251 of SEQ ID NO:5 (SY2726DQ), (3) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and an A allele at nucleotide 251 of SEQ ID NO:7 (SY2724CQ); (4) a T allele at nucleotide 251 of SEQ ID NO:1 (SY2723AQ), an A allele at nucleotide 251 of SEQ ID NO:5 (SY2726DQ), a G allele at nucleotide 251 of SEQ ID NO:8 (SY2725AQ), and a G allele at nucleotide 251 of SEQ ID NO:7 (SY2724CQ); or any combination thereof.

In some embodiments, the present invention provides methods of producing a soybean plant having an Rps1-a resistance allele and an Rps1-k resistance allele and/or an inbred soybean plant that is homozygous for an Rps1-a resistance allele and an Rps1-k resistance allele and/or methods for introgressing an Rps1-a resistance allele and an Rps1-k resistance allele into a soybean germplasm lacking the Rps1-a and Rps1-k resistance alleles, wherein the step of detecting the presence of a genetic marker associated with an Rps1-a resistance allele and an Rps1-k resistance allele, comprises detecting the presence of the genetic marker comprising: (1) a T allele at nucleotide 251 of SEQ ID NO:1 (SY2723AQ) and an A allele at nucleotide 251 of SEQ ID NO:8 (SY2725AQ); (2) a T allele at nucleotide 251 of SEQ ID NO:1 (SY2723AQ), a G allele at nucleotide 251 of SEQ ID NO:3 (SY2724AQ) and an A allele at nucleotide 251 of SEQ ID NO:8 (SY2725AQ); (3) a T allele at nucleotide 251 of SEQ ID NO:1 (SY2723AQ), an C allele at nucleotide 251 of SEQ ID NO:5 (SY2726DQ) and an A allele at nucleotide 251 of SEQ ID NO:8 (SY2725AQ); (4) a T allele at nucleotide 251 of SEQ ID NO:1 (SY2723AQ), a G allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (5) a T allele at nucleotide 251 of SEQ ID NO:1 (SY2723AQ), a G allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (6) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ); (7) a T allele at nucleotide 251 of SEQ ID NO:1 (SY2723AQ), a C allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (8) a T allele at nucleotide 251 of SEQ ID NO:1 (SY2723AQ), a C allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); or any combination thereof.

In some embodiments, the present invention provides methods of producing a soybean plant having an Rps1-c resistance allele and an Rps1-k resistance allele and/or an inbred soybean plant that is homozygous for an Rps1-c resistance allele and an Rps1-k resistance allele and/or methods for introgressing an Rps1-c resistance allele and an Rps1-k resistance allele into a soybean germplasm lacking the Rps1-c and Rps1-k resistance alleles, wherein the step of detecting the presence of a genetic marker associated with an Rps1-c resistance allele and an Rps1-k resistance allele, comprises detecting the presence of the genetic marker comprising: (a) an A allele at nucleotide 251 of SEQ ID NO:6 (SY2724BQ); (b) an A allele at nucleotide 251 of SEQ ID NO:7 (SY2724CQ); (3) C allele at nucleotide 251 of SEQ ID NO:3 (SY2724AQ) and an A allele at nucleotide 251 of SEQ ID NO:8 (SY2725AQ); (4) an A allele at nucleotide 251 of SEQ ID NO:5 (SY2726DQ) and an A allele at nucleotide 251 of SEQ ID NO:8 (SY2725AQ); (5) a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (6) a C allele at nucleotide 251 of SEQ ID NO:3 (SY2724AQ), a G allele at nucleotide 251 of SEQ ID NO:8 (SY2725AQ) and an A allele at nucleotide 251 of SEQ ID NO:7 (SY2724CQ); (7) an A allele at nucleotide 251 of SEQ ID NO:5 (SY2726DQ), an A allele at nucleotide 251 of SEQ ID NO:8 (SY2725AQ) and an A allele at nucleotide 251 of SEQ ID NO:7 (SY2724CQ; (8) an A allele at nucleotide 251 of SEQ ID NO:5 (SY2726DQ), a G allele at nucleotide 251 of SEQ ID NO:8 (SY2725AQ) and an A allele at nucleotide 251 of SEQ ID NO:7 (SY2724CQ); (9) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); (10) an A allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and a G allele at nucleotide 251 of SEQ ID NO:7 (SY2724CQ); or any combination thereof.

In other embodiments, the present invention provides methods of producing a soybean plant having an Rps1-a resistance allele, an Rps1-c resistance allele and an Rps1-k resistance allele and/or an inbred soybean plant that is homozygous for an Rps1-a resistance allele, an Rps1-c resistance allele and an Rps1-k resistance allele and/or methods for introgressing an Rps1-a resistance allele, an Rps1-c resistance allele and an Rps1-k resistance allele into a soybean germplasm lacking the Rps1-a, Rps1-c, and Rps1-k resistance alleles, wherein the step of detecting the presence of a genetic marker associated with an Rps1-a resistance allele, an Rps1-c resistance allele and an Rps1-k resistance allele, comprises detecting the presence of the genetic marker comprising: (1) a T allele at nucleotide 251 of SEQ ID NO:1 (SY2723AQ), a C allele at nucleotide 251 of SEQ ID NO:3 (SY2724AQ) and an A allele at nucleotide 251 of SEQ ID NO:8 (SY2725AQ), (2) a T allele at nucleotide 251 of SEQ ID NO:1 (SY2723AQ), an A allele at nucleotide 251 of SEQ ID NO:5 (SY2726DQ), and an A allele at nucleotide 251 of SEQ ID NO:8 (SY2725AQ); (3) a T allele at nucleotide 251 of SEQ ID NO:1 (SY2723AQ), is a C allele at nucleotide 251 of SEQ ID NO:3 (SY2724AQ), an A allele at nucleotide 251 of SEQ ID NO:8 (SY2725AQ) and an A allele at nucleotide 251 of SEQ ID NO:7 (SY2724CQ); (4) a T allele at nucleotide 251 of SEQ ID NO:1 (SY2723AQ), an A allele at nucleotide 251 of SEQ ID NO:5 (SY2726DQ), an A allele at nucleotide 251 of SEQ ID NO:8 (SY2725AQ), and an A allele at nucleotide 251 of SEQ ID NO:7 (SY2724CQ); or any combination thereof.

Soybean Plants, Parts Thereof, and Germplasms Having Rps1 Resistance Alleles

The present invention provides soybean plants and germplasms having Rps1 resistance alleles (e.g., Rps1-a, Rps1-c, and/or Rps1-k) and resistance to *P. sojae*. As discussed above, the methods of the present invention can be utilized to identify, produce and/or select a soybean plant or germplasm having an Rps1 resistance allele. In addition to the methods described above, a soybean plant or germplasm having an Rps1 resistance allele may be produced by any method whereby a marker associated with an Rps1 resistance allele is introduced into the soybean plant or germplasm by such methods that include, but are not limited to, transformation (including, but not limited to, bacterial-mediated nucleic acid delivery (e.g., via *Agrobacteria*)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof), protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a soybean plant, or part thereof, having an Rps1 resistance allele (i.e., *P. sojae*-resistant soybean plant or part thereof), obtainable by the methods of the presently disclosed subject matter, are aspects of the presently disclosed subject matter. In some embodiments, the soybean plant of the present invention has more than one Rps1 resistance allele as described herein.

The soybean plant, or part thereof, of this invention having an Rps1 resistance allele can be heterozygous or homozygous for the resistance allele. In some embodiments of this invention, the soybean plant has more than one Rps1 resistance allele and thus, can be heterozygous at some Rps1 resistance alleles and homozygous at other Rps1 resistance alleles.

The soybean plant or germplasm may be the progeny of a cross between a variety of soybean and a second variety of soybean that comprises an Rps1 resistance allele.

The soybean plant or germplasm may be the progeny of an introgression wherein the recurrent parent is a variety of soybean and the donor comprises an Rps1 resistance allele.

The soybean plant or germplasm may be the progeny of a cross between a first variety of soybean (e.g., a tester line) and the progeny of a cross between a second variety of soybean (e.g., a recurrent parent) and a variety of soybean that comprises an Rps1 resistance allele (e.g., a donor).

The soybean plant or germplasm may be the progeny of a cross between a first variety of soybean and the progeny of an introgression wherein the recurrent parent is a second variety of soybean and the donor comprises an Rps1 resistance allele.

Another aspect of the presently disclosed subject matter relates to a method of producing seeds that can be grown into *P. sojae*-resistant soybean plants. In some embodiments, the method comprises providing a *P. sojae*-resistant soybean plant of this invention, crossing the *P. sojae*-resistant plant with another soybean plant, and collecting seeds resulting from the cross, which when planted, produce *P. sojae*-resistant soybean plants.

Accordingly, the present invention provides improved soybean plants, seeds, and/or tissue cultures produced by the methods described herein. In further embodiments, the present invention provides introgressed *Glycine max* plants and/or germplasm produced by the methods described herein.

Compositions for Analysis of a Soybean Genome

In some embodiments, the presently disclosed subject matter provides methods for analyzing the genomes of soybean plants/germplasms to identify those that include desired markers associated with *P. sojae* resistance. In some embodiments, the methods of analysis comprise amplifying subsequences of the genomes of the soybean plants/germplasms and determining the nucleotides present in one, some, or all positions of the amplified subsequences.

Thus, in some embodiments, the present invention provides compositions comprising one or more amplification primer pairs capable of initiating DNA polymerization by a DNA polymerase on a *Glycine max* nucleic acid template to generate a *Glycine max* marker amplicon. In some embodiments, the *Glycine max* amplicon can be used to identify the *Glycine max* marker comprising a nucleotide sequence of any of SEQ ID NOs: 1-8. In view of the disclosure of SEQ ID NOs: 1-8 as being linked to pathogen resistance loci, one of ordinary skill in the art would be aware of various techniques that could be employed to analyze the sequences of the corresponding soybean nucleic acids. Representative amplification primer pairs can comprise the nucleotide sequences of a forward primer and corresponding reverse primer as set forth hereinabove in Table 1.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1. Soybean Lines

To determine and validate the accuracy of the eight SNP markers (set forth in Table 1) for detecting the Rps-1 resistance alleles, Rps1a, Rps1c, Rps1k, and susceptible allele, 337 Syngenta soybean lines were selected. Among the 337 lines, 82 lines carry Rps1a, 82 lines contain Rps1c, 81 lines have Rps1k, and 92 lines are susceptible to *P. sojae* (see, Table 2).

Example 2. Screening for *Phytopthora Sojae* Resistance in Soybean

Zoospores of *P. sojae* were obtained by transferring peripheral disks from young colonies (3-4 days old) to a new plate and incubating them for 24 h at 21° C. with intermittent washings (3-4 washes or as needed) with sterilized distilled water to promote sporangia production. After overnight incubation zoospores were released from sporangia that are collected, counted in hemacytometer, and diluted to the required concentration.

Four inch square pots filled with vermiculate were planted with 20 soybean seeds, which are allowed to germinate. Young seedlings of soybean (5-7 days old) were inoculated with 20,000 zoospres/ml using syringe (30G) by making a slit in the hypocotyls of the plant and placing a droplet of the zoospore suspension. Seedlings were incubated in a growth chamber at 21° C. for about 7 days post inoculation under 12-14 h light and then moved to greenhouse and maintained at 24° C. with 12-14 h light conditions for another 3-5 days before rating for disease. Susceptible (hosts) plants develop distinctive symptoms and died 3-5 days after inoculation. Resistant (non-host) plants develop hypersensitive reaction and the symptom development fails to progress beyond the site of inoculation. Less than 25% of the plants that die from *P. sojae* are resistant; 26 to 75% of the plants that die are intermediate in resistance; and greater than 75% of the plants that die from *P. sojae* infection are susceptible. An intermediate reaction can either indicate contamination of the soybean line or a mixed culture of the pathotype. Respective differential checks are used as controls to validate the purity of the pathotype. The Rps1 resistance alleles 1a, 1c, 1k and susceptible rps1 in soybean lines were determined based on host-pathogen interactions as shown in Table 3, below. Using this method, the Rps1 alleles in 337 soybean lines were identified, which were selected for further research (See, e.g., Table 1).

TABLE 3

Response of different *P. sojae* races to Rps1 resistance alleles.

| | *P. sojae* races (pathotypes) | | | | | | |
|---|---|---|---|---|---|---|---|
| gene (s) | 1 | 2 | 3 | 4 | 7 | 25 | 31 | OH8 |
| Rps1a | R | R | S | S | S | S | R | R |
| Rps1c | R | R | R | S | R | S | R | R |
| Rps1k | R | R | R | R | R | S | S | R |
| Susceptible rps1 | S | S | S | S | S | S | S | S |

Example 3. SNP Genotyping

The tissue from each soybean line was obtained by growing the plants in the field or greenhouse. DNA was extracted from the leaf tissue of 7-10 day old seedlings (7-10 days after planting). DNA can be extracted from plant tissue in any way known in the art, including the CTAB (hexadecyltrimethylammonium bromide) method (See, e.g., Stewart et al., *BioTechniques* 14(5):748-749 (1993)), sodium hydroxide, and the Dellaporta method (Dellaporta et al., *Plant Mol. Biol. Rep.* 1:19-21 (1983)). Additional art known methods of DNA extraction also can be used (See, e.g., Sambrook & Russell *Molecular Cloning: A Laboratory Manual, Third Edition*, Cold Spring Harbor Laboratory Press, Cold Spring Harbor, N.Y., United States of America (2001)). DNA is diluted in TE buffer and stored at 4° C. for use in PCR reactions as described below in Table 4.

TABLE 4

PCR was set up in 5 μl final volumes according to the following formula.

| Reagent | Stock concentration | Per reaction (μl) | For 96 samples (μl) | Final concentration |
|---|---|---|---|---|
| 2X Master Mix (JumpStart ™ Taq ReadyMix ™) | 2X | 2.5 | 296.88 | 1X |
| AbD primer/probe mix (80x) | 40x | .0625 | 6 | 0.5x |
| PCR-quality H2O | — | 2.44 | 234.24 | — |
| DNA (dried in 384) | 4.5 ng/μl | 4 | — | 3.6 ng/ul (18ng) |
| Final Volume (ul) | | 5.00 | 357.44 | |

The Master Mix is JumpStart™ Taq ReadyMix™ (Sigma Catologue No. 2893; Sigma Chemical Co., St. Louis, Mo., United States of America), a premix of all the components, including nucleotides and Taq polymerase (not including the primers or probes) necessary to perform a 5'-nuclease assay. Before use, 1375 μl of 1.0 M $MgCl_2$ (Sigma Catalogue No. M1028) and 250 μl of 300 μM Sulforhodamine 101 (Sigma Catalogue No. S7635), also known as ROX, are added to a 125 mL bottle of JumpStart™ Taq ReadyMix™. PCR plates were placed in an ABI 9700 thermal cycler and the program set forth in Table 5 was run:

TABLE 5

PCR program.

| Task | SNP1 |
|---|---|
| Initial denaturation | 50° C. for 2 min; followed by 95° C. for 10 min |
| Cycles | 95° C. for 15 sec |
|  | 60° C. for 1 min |
| Number of cycles | 40 |
| Final elongation | 72° C. for 5 min |
| Hold | Hold at 4° C. |

The ABI 7900 Sequence Detection System (or Taqman®) was used to visualize the results of an allelic discrimination (SNP) assay. Using the Sequence Detection System (SDS) software, allele calls were made based on the fluorescence for the two dyes measured in each sample.

Example 4. Validation of SNP Markers for Rps1a, Rps1c, Rps1k, and Susceptible Allele in Soybean The eight SNP markers as shown in Table 1 were validated for the Rps1-a, Rps1-c, Rps1-1k, and/or susceptible allele in 337 soybean lines. The results are set forth in Table 6 and confirmed the phenotypic data (Example 4).

TABLE 6

Validation of eight SNP markers for Rps1a, Rps1c, Rps1k, and susceptible allele in 337 soybean lines.

| Soybean Line | Rps1 allele | SY2723AQ (A/T) | SY2721AQ (A/C) | SY2724AQ (C/G) | SY2726BQ (C/G) | SY2726DQ (A/C) | SY2724BQ (A/G) | SY2724CQ (A/G) | SY2725AQ (A/G) |
|---|---|---|---|---|---|---|---|---|---|
| AR0800164 | 1A | T | A | G | C | C | G | G | G |
| NE0800402 | 1A | T | C | G | C | C | G | G | G |
| BK0800608 | 1A | T | C | G | C | C | G | G | G |
| S48-C9 | 1A | T | C | G | — | H | G | — | G |
| BN0810632 | 1A | T | C | G | C | C | G | G | G |
| BN0810574 | 1A | T | C | G | C | C | G | G | G |
| OW0810225 | 1A | T | C | G | C | C | G | G | G |
| OW0810227 | 1A | T | C | G | C | C | G | G | G |
| OW0810261 | 1A | T | C | G | C | C | G | G | G |
| OW0810211 | 1A | T | C | G | C | C | G | G | G |
| NE0800396 | 1A | T | C | G | C | C | G | G | G |
| NE0800405 | 1A | T | A | G | C | C | G | G | G |
| NE0800408 | 1A | T | A | G | C | C | G | G | G |
| NE0800447 | 1A | T | C | G | C | C | G | G | G |
| NE0800450 | 1A | T | C | G | C | C | G | G | G |
| NE0800452 | 1A | T | C | G | C | C | G | G | G |
| WN0810484 | 1A | T | C | G | C | C | G | G | G |
| XR3201 | 1A | T | C | G | C | C | G | G | G |
| WN0800538 | 1A | T | C | G | C | C | G | G | G |
| WN0800547 | 1A | T | C | G | C | C | G | G | G |
| WN0800570 | 1A | T | C | G | C | C | G | G | G |
| WN0800576 | 1A | T | C | G | C | C | G | G | G |
| BK0810186 | 1A | T | C | G | C | C | G | G | G |
| HI0810776 | 1A | T | C | G | C | C | G | G | G |
| NE0810334 | 1A | T | H | G | C | C | G | G | G |
| S19-V2 | 1A | T | C | G | C | C | G | G | G |
| OW0810298 | 1A | T | C | G | C | C | G | G | G |
| GO0800735 | 1A | T | C | G | C | C | G | G | G |
| SJ0800051 | 1A | T | C | G | C | C | G | G | G |
| WN0810620 | 1A | T | C | G | C | C | G | G | G |
| BN0810584 | 1A | T | C | G | C | C | G | G | G |
| SJ0800206 | 1A | T | C | G | C | C | G | G | G |
| SJ0810655 | 1A | T | C | G | C | C | G | G | G |
| WN0810659 | 1A | T | C | G | C | C | G | G | G |
| WN0810614 | 1A | T | C | G | C | C | G | G | G |
| WN0800534 | 1A | T | C | G | C | C | G | G | G |
| WN0800539 | 1A | T | C | G | C | C | G | G | G |
| WN0800556 | 1A | T | C | G | C | — | G | G | G |
| WN0800558 | 1A | T | C | G | C | C | G | G | G |
| WN0800564 | 1A | T | C | G | C | C | G | G | G |
| HI0800661 | 1A | T | H | G | C | C | G | G | G |
| BY0810791 | 1A | T | C | G | C | C | G | G | G |
| SJ0810773 | 1A | T | C | G | C | C | G | G | G |
| SJ0810828 | 1A | T | C | G | C | C | G | G | G |
| HI0810825 | 1A | T | C | G | C | C | G | G | G |
| HI0810742 | 1A | T | C | G | C | C | G | G | G |
| XR4317 | 1A | T | C | G | C | C | G | G | G |
| BN0800121 | 1A | T | C | G | C | C | G | G | G |
| HI0800685 | 1A | T | C | G | C | C | G | G | G |
| S10-K1 | 1A | T | C | G | C | C | G | G | G |
| S00-W3 | 1A | T | A | G | C | C | G | G | G |
| S15-B1 | 1A | T | C | G | H | H | G | — | G |
| S21-H3 | 1A | T | C | G | C | C | G | G | G |
| S36-B6 | 1A | T | C | G | C | C | G | G | G |
| S30-D4 | 1A | T | C | G | C | C | G | G | G |
| S23-N7 | 1A | T | C | G | C | C | G | G | G |
| S34-R2 | 1A | T | C | G | C | C | G | G | G |
| S30-F5 | 1A | T | C | G | C | C | G | G | G |

TABLE 6-continued

Validation of eight SNP markers for Rps1a, Rps1c, Rps1k, and susceptible allele in 337 soybean lines.

| Soybean Line | Rps1 allele | SY2723AQ (A/T) | SY2721AQ (A/C) | SY2724AQ (C/G) | SY2726BQ (C/G) | SY2726DQ (A/C) | SY2724BQ (A/G) | SY2724CQ (A/G) | SY2725AQ (A/G) |
|---|---|---|---|---|---|---|---|---|---|
| S31-H9 | 1A | T | C | G | C | C | G | G | G |
| S33-K5 | 1A | T | C | G | C | C | G | G | G |
| SJ0800048 | 1A | T | C | G | C | C | G | G | G |
| SJ0800052 | 1A | T | C | G | C | C | G | G | G |
| XR3192 | 1A | T | C | G | C | C | G | G | G |
| SJ0800227 | 1A | T | C | G | C | C | G | G | G |
| SJ0800213 | 1A | T | C | G | C | C | G | G | G |
| HI0800614 | 1A | T | C | G | C | C | G | G | G |
| SJ0800047 | 1A | T | A | G | C | C | G | G | G |
| SJ0810784 | 1A | T | C | G | C | — | G | G | G |
| BN0810737 | 1A | T | C | G | C | C | G | G | G |
| S23-H2 | 1A | T | C | G | C | C | G | G | G |
| S25-B9 | 1A | T | C | G | C | C | G | G | G |
| S27-L4 | 1A | T | C | G | C | C | G | G | G |
| S29-J6 | 1A | T | C | G | C | C | G | G | G |
| S19-R5 | 1A | T | C | G | C | C | G | G | G |
| S00-A6 | 1A | T | C | G | C | C | G | G | G |
| S23-Z3 | 1A | T | C | G | C | C | G | G | G |
| S28-G1 | 1A | T | C | G | C | C | G | G | G |
| S22-F5 | 1A | T | C | G | C | C | G | G | G |
| S32-E2 | 1A | T | C | G | C | C | G | G | G |
| S00-Z1 | 1A | T | A | G | C | C | G | G | G |
| BN0810573 | 1A | T | C | G | C | C | G | G | G |
| BN0810700 | 1A | T | C | G | C | C | G | G | G |
| S36-J4 | 1C | A | C | C | G | A | A | A | G |
| XR1707 | 1C | A | C | C | G | A | A | A | G |
| AR0800193 | 1C | A | A | C | G | A | A | A | G |
| WW221162 | 1C | A | C | C | G | A | A | A | G |
| OW0800388 | 1C | A | C | C | G | A | A | A | G |
| S02-M9 | 1C | A | C | C | G | A | A | A | G |
| 05BR047009 | 1C | A | C | C | G | A | A | A | G |
| BN0810695 | 1C | A | C | C | G | A | A | A | G |
| BN0810688 | 1C | A | C | C | G | A | A | A | G |
| BN0810641 | 1C | A | C | C | G | A | A | A | G |
| S49-F4 | 1C | A | C | C | G | A | — | A | G |
| S51-T8 | 1C | A | C | C | G | — | A | A | G |
| S50-N3 | 1C | A | H | C | H | A | — | A | G |
| S54-G9 | 1C | A | C | C | G | A | A | A | G |
| S49-T1 | 1C | A | C | C | G | A | A | A | G |
| S10-B7 | 1C | A | C | C | G | A | A | A | G |
| XR0790 | 1C | A | C | C | G | A | A | A | G |
| OW0810046 | 1C | A | C | C | G | A | — | — | G |
| GO0810012 | 1C | A | C | C | G | A | A | A | G |
| GO0810004 | 1C | A | C | C | G | A | A | A | G |
| GO0810013 | 1C | A | C | C | G | A | A | A | G |
| GO0810083 | 1C | A | C | C | G | A | A | A | G |
| S00-J9 | 1C | A | C | C | G | A | A | A | G |
| GO0810108 | 1C | A | C | C | G | A | A | A | G |
| BK0810126 | 1C | A | C | C | G | A | A | A | G |
| OW0810085 | 1C | A | A | C | G | A | A | A | G |
| S00-H7 | 1C | A | C | C | G | A | A | A | G |
| XR0304 | 1C | A | C | C | G | A | A | A | G |
| S04-Z9 | 1C | A | C | C | G | A | A | A | G |
| S08-C3 | 1C | A | C | C | G | A | A | A | G |
| XR0202 | 1C | A | C | C | G | A | A | A | G |
| BN0810836 | 1C | A | C | C | G | A | — | A | G |
| HI0810829 | 1C | A | C | C | G | A | A | A | G |
| HI0810818 | 1C | A | C | C | G | A | — | — | A | G |
| HI0810800 | 1C | A | C | C | G | A | A | A | G |
| HI0810826 | 1C | A | C | C | G | A | A | A | G |
| HI0810830 | 1C | A | C | C | G | A | — | A | G |
| HI0810837 | 1C | A | C | C | G | A | A | A | G |
| HI0810819 | 1C | A | H | C | H | — | H | A | G |
| S05-T6 | 1C | A | C | C | G | A | A | A | G |
| S20-G7 | 1C | A | C | C | G | A | A | A | G |
| S17-B5 | 1C | A | C | C | G | A | A | A | G |
| S08-A2 | 1C | A | C | C | G | A | A | A | G |
| S09-N6 | 1C | A | C | C | G | A | A | A | G |
| S15-R2 | 1C | A | C | C | G | A | A | A | G |
| S11-L2 | 1C | A | C | C | G | A | A | A | G |
| S14-A7 | 1C | A | C | C | G | A | A | A | G |
| S16-C4 | 1C | A | C | C | G | A | A | A | G |
| S14-K6 | 1C | A | C | C | G | A | A | A | G |
| S17-P9 | 1C | A | C | C | G | A | A | A | G |

TABLE 6-continued

Validation of eight SNP markers for Rps1a, Rps1c, Rps1k, and susceptible allele in 337 soybean lines.

| Soybean Line | Rps1 allele | SY2723AQ (A/T) | SY2721AQ (A/C) | SY2724AQ (C/G) | SY2726BQ (C/G) | SY2726DQ (A/C) | SY2724BQ (A/G) | SY2724CQ (A/G) | SY2725AQ (A/G) |
|---|---|---|---|---|---|---|---|---|---|
| S13-Y3 | 1C | A | C | C | G | A | A | A | G |
| S03-B2 | 1C | A | A | H | G | A | A | A | G |
| S12-P4 | 1C | A | C | C | G | A | A | A | G |
| S12-C2 | 1C | A | C | C | G | A | — | A | G |
| S21-V9 | 1C | A | C | C | G | A | A | A | G |
| S44-J5 | 1C | A | C | C | G | A | A | A | G |
| S47-D9 | 1C | A | C | C | G | A | A | A | G |
| S43-N6 | 1C | A | C | C | G | A | A | A | G |
| S46-U6 | 1C | A | C | C | G | A | A | A | G |
| S33-T4 | 1C | A | C | C | G | A | A | A | G |
| S44-D5 | 1C | A | C | C | G | A | A | A | G |
| S23-T5 | 1C | A | C | C | G | A | A | A | G |
| S22-C5 | 1C | A | C | C | G | A | A | A | G |
| S38-H8 | 1C | A | C | C | G | A | A | A | G |
| BN0800119 | 1C | A | C | C | G | A | A | A | G |
| SJ0800222 | 1C | A | C | C | G | A | A | A | G |
| S49-Q9 | 1C | A | C | C | G | A | A | A | G |
| S06-D9 | 1C | A | C | C | G | A | A | A | G |
| S01-T5 | 1C | A | C | C | G | A | A | A | G |
| S38-T8 | 1C | A | C | C | G | A | A | A | G |
| S35-F9 | 1C | A | C | C | G | A | A | A | G |
| S39-Q4 | 1C | A | C | C | G | A | A | A | G |
| S21-D2 | 1C | A | C | C | G | A | A | A | G |
| S36-C7 | 1C | A | C | C | G | A | A | A | G |
| S38-D5 | 1C | A | C | C | G | A | A | A | G |
| NK 35-00 RR | 1C | A | C | C | G | A | A | A | G |
| S37-N4 | 1C | A | C | C | G | A | A | A | G |
| S34-U4 | 1C | A | C | C | G | A | A | A | G |
| S43-B1 | 1C | A | C | C | G | A | A | A | G |
| S28-Y2 | 1C | A | C | C | G | A | A | A | G |
| S30-J8 | 1C | A | C | C | G | A | A | A | G |
| AR0800190 | 1K | A | A | G | C | H | A | A | A |
| OW0800382 | 1K | A | A | G | C | C | A | A | A |
| S14-N1 | 1K | A | A | G | C | C | A | A | A |
| S29-W7 | 1K | A | A | G | C | C | A | A | A |
| WN0810530 | 1K | A | A | G | C | C | A | A | A |
| XR1892 | 1K | A | A | G | C | C | A | A | A |
| NE0800095 | 1K | A | A | G | C | C | A | A | A |
| S23-A8 | 1K | A | A | G | C | C | A | A | A |
| BN0810534 | 1K | A | A | G | C | C | A | A | A |
| BN0810542 | 1K | A | A | G | C | C | A | A | A |
| OW0810238 | 1K | A | A | G | C | C | A | A | A |
| OW0810183 | 1K | A | A | G | G | A | A | A | G |
| OW0800371 | 1K | A | A | G | C | C | A | A | A |
| OW0800373 | 1K | A | A | G | C | C | A | A | A |
| OW0800366 | 1K | A | A | G | C | C | A | A | A |
| 03JR101916 | 1K | A | A | G | C | C | A | A | A |
| BN0810711 | 1K | A | C | C | G | A | A | A | G |
| SJ0810677 | 1K | A | A | G | C | C | A | A | A |
| SJ0810678 | 1K | A | A | G | C | C | A | A | A |
| SJ0810705 | 1K | A | A | G | C | C | A | A | A |
| HI0800665 | 1K | A | C | C | G | A | A | A | G |
| HI0800672 | 1K | A | A | G | C | C | A | A | A |
| HI0800688 | 1K | A | A | G | C | C | A | A | A |
| HI0810907 | 1K | A | A | G | C | C | A | A | A |
| S01-C9 | 1K | A | A | G | C | C | — | A | A |
| S02-K3 | 1K | A | A | G | C | C | A | A | A |
| S25-R3 | 1K | A | A | G | C | C | A | A | A |
| OW0800083 | 1K | A | A | G | C | C | A | A | A |
| XR00991 | 1K | A | A | C | G | A | A | A | G |
| OW0800367 | 1K | A | A | G | C | C | A | A | A |
| OW0800372 | 1K | A | A | G | C | C | A | A | A |
| GO0810084 | 1K | A | A | G | C | C | A | A | A |
| 03JR313108 | 1K | A | A | G | C | C | A | A | A |
| 03KL015751 | 1K | A | A | G | C | C | A | A | A |
| BN0810811 | 1K | A | A | G | C | C | A | A | A |
| HI0810846 | 1K | A | H | C | H | A | A | A | — |
| HI0810890 | 1K | A | A | G | C | C | A | A | A |
| HI0800643 | 1K | A | A | G | C | C | A | A | A |
| HI0800690 | 1K | A | A | G | C | C | A | A | A |
| HI0800674 | 1K | A | A | G | C | C | A | A | A |
| HI0800675 | 1K | A | A | G | C | C | A | A | A |
| HI0800691 | 1K | A | A | G | C | C | A | A | A |
| S14-C5 | 1K | A | A | G | C | C | A | A | A |
| S13-K2 | 1K | A | A | G | C | C | — | — | A |

TABLE 6-continued

Validation of eight SNP markers for Rps1a, Rps1c, Rps1k, and susceptible allele in 337 soybean lines.

| Soybean Line | Rps1 allele | SY2723AQ (A/T) | SY2721AQ (A/C) | SY2724AQ (C/G) | SY2726BQ (C/G) | SY2726DQ (A/C) | SY2724BQ (A/G) | SY2724CQ (A/G) | SY2725AQ (A/G) |
|---|---|---|---|---|---|---|---|---|---|
| S13-A4 | 1K | A | A | G | C | C | A | A | A |
| S11-J8 | 1K | A | A | G | C | C | A | A | A |
| S21-N6 | 1K | A | C | C | G | A | A | A | G |
| S13-J9 | 1K | A | C | G | C | C | A | A | A |
| S11-R6 | 1K | A | A | G | C | C | A | A | A |
| S23-C2 | 1K | A | A | G | C | C | A | A | A |
| S10-T1 | 1K | A | A | G | H | H | A | A | — |
| S45-E5 | 1K | A | A | G | C | C | A | A | A |
| S28-B4 | 1K | A | A | G | C | C | A | A | A |
| S24-J1 | 1K | A | A | G | C | C | A | A | A |
| S27-C4 | 1K | A | A | G | C | C | A | A | A |
| S32-N9 | 1K | A | A | G | C | C | A | A | A |
| S26-P1 | 1K | A | A | G | C | C | A | A | A |
| XR3493 | 1K | A | A | G | C | C | A | A | A |
| SJ0810631 | 1K | A | A | G | C | C | A | A | A |
| SJ0800018 | 1K | A | A | G | C | C | A | A | A |
| NE0800088 | 1K | A | A | G | C | C | A | A | A |
| WN0800106 | 1K | A | A | G | C | C | A | A | A |
| BN0810561 | 1K | A | A | G | C | C | A | A | A |
| HI0800667 | 1K | A | A | G | C | C | — | A | A |
| HI0800677 | 1K | A | C | C | G | A | A | A | G |
| HI0800682 | 1K | A | A | G | C | C | A | A | A |
| HI0810765 | 1K | A | A | G | C | C | A | A | A |
| HI0810713 | 1K | A | A | G | C | C | A | A | A |
| BN0810753 | 1K | A | C | C | G | A | A | A | G |
| BN0810745 | 1K | A | C | C | G | A | A | A | G |
| BN0810788 | 1K | A | A | G | C | C | A | A | A |
| BN0810767 | 1K | A | A | G | C | C | A | A | A |
| SJ833009 | 1K | A | A | G | C | C | A | A | A |
| S28-E6 | 1K | A | A | — | C | C | A | A | A |
| S34-K1 | 1K | A | A | G | C | C | A | A | A |
| S24-K6 | 1K | A | A | G | C | C | A | A | A |
| XR3090 | 1K | A | A | G | C | C | A | A | A |
| XR3191 | 1K | A | A | G | C | C | A | A | A |
| XR4090 | 1K | A | A | G | C | C | A | A | A |
| XR2090 | 1K | A | A | G | C | C | A | A | A |
| S12-U7 | 1K | A | A | G | C | C | A | A | A |
| BN0810762 | SUSC | A | A | G | C | C | G | G | G |
| BN0810763 | SUSC | A | A | G | C | C | G | G | G |
| BY0811028 | SUSC | A | A | G | C | C | G | G | G |
| OW0800357 | SUSC | A | A | G | C | C | G | G | G |
| HI0810916 | SUSC | A | A | G | C | C | G | G | G |
| HI0810801 | SUSC | A | A | G | C | C | G | G | G |
| 03RM893031 | SUSC | A | A | G | C | C | G | — | — |
| SJ0800026 | SUSC | A | A | G | C | C | G | G | G |
| SJ0800032 | SUSC | A | A | G | C | C | G | G | G |
| WN0800102 | SUSC | A | A | G | C | C | G | G | G |
| BN0810627 | SUSC | A | A | G | C | C | G | G | G |
| BN0810673 | SUSC | A | A | G | C | C | G | G | G |
| BN0810653 | SUSC | A | A | G | H | H | G | — | G |
| SJ0800208 | SUSC | A | A | G | C | C | G | G | G |
| SJ0810679 | SUSC | A | A | G | C | C | G | G | — |
| SJ0810611 | SUSC | A | A | G | C | C | G | G | G |
| HI0800616 | SUSC | A | A | G | C | C | G | G | G |
| HI0800650 | SUSC | T | A | G | C | C | G | G | G |
| HI0800662 | SUSC | T | A | G | C | C | G | G | G |
| HI0800669 | SUSC | A | A | G | C | C | G | G | G |
| BY0810934 | SUSC | A | A | G | C | C | G | G | G |
| BY0810924 | SUSC | A | A | G | C | C | G | G | G |
| BY0810920 | SUSC | A | A | G | C | C | G | G | G |
| BY0810956 | SUSC | A | A | G | C | C | G | G | G |
| BY0810900 | SUSC | A | A | G | C | C | G | G | G |
| BY0810925 | SUSC | A | A | G | H | H | G | — | G |
| BY0810865 | SUSC | A | A | G | C | C | G | G | G |
| BY0810951 | SUSC | A | A | G | C | C | G | G | G |
| BY0810999 | SUSC | A | A | G | C | C | G | G | G |
| BY0810908 | SUSC | A | A | G | C | C | G | G | G |
| BY0810913 | SUSC | A | A | G | C | C | G | G | G |
| BY0810930 | SUSC | A | A | G | C | C | G | G | G |
| BY0810946 | SUSC | A | A | G | C | C | G | G | G |
| BY0810857 | SUSC | A | A | G | C | C | G | G | G |
| BY0810887 | SUSC | A | A | G | — | — | G | G | G |
| BY0811062 | SUSC | A | A | G | C | C | G | G | G |
| HI0810954 | SUSC | A | A | G | C | C | G | G | G |
| OW0800338 | SUSC | A | A | G | C | C | G | G | G |

TABLE 6-continued

Validation of eight SNP markers for Rps1a, Rps1c, Rps1k, and susceptible allele in 337 soybean lines.

| Soybean Line | Rps1 allele | SY2723AQ (A/T) | SY2721AQ (A/C) | SY2724AQ (C/G) | SY2726BQ (C/G) | SY2726DQ (A/C) | SY2724BQ (A/G) | SY2724CQ (A/G) | SY2725AQ (A/G) |
|---|---|---|---|---|---|---|---|---|---|
| OW0800341 | SUSC | A | A | G | C | C | G | G | G |
| BN0810797 | SUSC | A | A | G | C | C | G | G | G |
| BY0810850 | SUSC | A | A | G | — | H | G | — | G |
| HI0800617 | SUSC | A | A | G | C | C | G | G | G |
| HI0800621 | SUSC | A | A | G | C | C | G | G | G |
| HI0800624 | SUSC | A | A | G | C | C | G | G | — |
| HI0800625 | SUSC | A | A | G | C | C | G | G | G |
| HI0800626 | SUSC | A | A | G | C | C | G | G | G |
| HI0810803 | SUSC | A | A | G | C | C | G | G | G |
| HI0810795 | SUSC | A | A | G | C | C | G | G | G |
| HI0810775 | SUSC | T | A | G | C | C | G | G | G |
| HI0810841 | SUSC | A | A | G | C | C | G | G | G |
| HI0800666 | SUSC | T | A | G | C | C | G | G | G |
| HI0800687 | SUSC | A | A | G | C | C | G | G | G |
| HI0800613 | SUSC | A | A | G | C | C | G | G | G |
| HI0800637 | SUSC | T | A | G | C | C | G | G | G |
| HI0800630 | SUSC | A | A | G | C | C | G | G | G |
| HI0800620 | SUSC | A | A | G | C | C | G | G | G |
| HI0800619 | SUSC | A | A | G | C | C | G | G | G |
| HI0800670 | SUSC | T | H | G | C | C | G | G | G |
| HI0800618 | SUSC | T | A | G | C | C | G | G | G |
| SJ0810651 | SUSC | T | A | G | C | C | G | G | G |
| S12-B3 | SUSC | A | A | G | C | C | G | G | G |
| S12-T8 | SUSC | A | A | G | C | C | G | G | G |
| S08-M8 | SUSC | A | A | G | C | C | G | G | G |
| S35-T9 | SUSC | A | A | G | C | C | G | G | G |
| BN0810666 | SUSC | A | A | G | C | C | G | G | G |
| BN0800008 | SUSC | A | A | G | C | C | G | G | G |
| SJ0800020 | SUSC | A | A | G | C | C | G | G | G |
| OW0800084 | SUSC | A | A | G | C | C | G | G | G |
| WN0800100 | SUSC | A | A | G | C | C | G | G | G |
| BN0810560 | SUSC | A | A | G | C | C | G | G | G |
| BN0810633 | SUSC | A | A | G | C | C | G | G | G |
| BN0800118 | SUSC | A | A | G | C | C | G | G | G |
| HI0800631 | SUSC | A | A | G | C | C | G | G | G |
| HI0800636 | SUSC | A | A | G | C | C | G | G | G |
| HI0800638 | SUSC | A | A | G | C | C | G | G | G |
| HI0810743 | SUSC | A | A | G | C | C | G | G | G |
| HI0800647 | SUSC | T | A | G | C | C | G | G | G |
| HI0800651 | SUSC | T | A | G | C | C | G | G | G |
| HI0800652 | SUSC | A | A | G | C | C | G | G | G |
| HI0800657 | SUSC | T | A | G | C | C | G | G | G |
| BN0810790 | SUSC | A | A | G | C | C | G | G | G |
| BN0810768 | SUSC | A | A | G | C | C | G | G | G |
| BN0810730 | SUSC | A | A | G | C | C | G | G | G |
| HI0810782 | SUSC | A | A | G | — | H | G | G | G |
| HI0810786 | SUSC | A | A | G | C | C | G | G | G |
| HI0810714 | SUSC | A | A | G | C | C | G | G | G |
| HI0800628 | SUSC | A | A | G | C | C | G | G | G |
| HI0800629 | SUSC | H | A | G | C | C | G | G | G |
| HI0800654 | SUSC | A | A | G | C | C | G | G | G |
| NE0810532 | SUSC | H | A | G | C | C | G | G | G |
| XR3494 | SUSC | H | A | G | C | C | G | G | G |
| WN0800098 | SUSC | A | A | G | C | C | G | G | G |

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A method of producing a *Glycine max* plant that has improved resistance to *Phytophthora sojae* as compared to a control plant, the method comprising the steps of:

(a) isolating a nucleic acid from a *Glycine max* plant;

(b) detecting in the nucleic acid of (a) the presence of a genetic marker that is associated with improved resistance to *Phytophthora sojae* and is associated with Rps1-k, wherein the genetic marker comprises SY2725AQ (SEQ ID NO: 8) and further comprises an A allele at nucleotide 251 of SEQ ID NO:8, or is a marker closely linked thereto on Soybean Chromosome 3, wherein the marker closely linked thereto comprises at least one of an A allele at nucleotide 251 of SEQ ID NO:6 (SY2724BQ) or an A allele at nucleotide 251 of SEQ ID NO:7 (SY2724CQ);

(c) selecting a first *Glycine max* plant based on the presence of the genetic marker detected in (b);

(d) crossing a second *Glycine max* plant with the first *Glycine max* plant of (c) wherein, said second *Glycine max* plant does not comprise in its genome the genetic marker detected in (b); and (e) producing seed from the crossing of (d) and thereby producing a *Glycine max* plant that has improved resistance to *Phytophthora sojae* as compared to a control plant.

2. The method of claim 1, wherein the detecting comprises detecting at least one allelic form of a polymorphic simple sequence repeat (SSR) or a single nucleotide polymorphism (SNP).

3. The method of claim 1, wherein the second *Glycine max* plant is an elite soybean line.

4. The method of claim 1 further comprising the step of backcrossing the plants produced in (e).

5. The method of claim 1, wherein detecting includes detecting the genetic marker comprising the A allele at nucleotide 251 of SEQ ID NO:8.

6. The method of claim 5, wherein detecting includes detecting both of the A allele at nucleotide 251 of SEQ ID NO:6 (SY2724BQ) and the A allele at nucleotide 251 of SEQ ID NO:7 (SY2724CQ).

* * * * *